US010310073B1

(12) United States Patent
Santra et al.

(10) Patent No.: US 10,310,073 B1
(45) Date of Patent: Jun. 4, 2019

(54) SYSTEM AND METHOD FOR DETERMINING ENGAGEMENT LEVEL OF A HUMAN BEING USING A MILLIMETER-WAVE RADAR SENSOR

(71) Applicant: Infineon Technologies AG, Neubiberg (DE)

(72) Inventors: Avik Santra, Munich (DE); Ashutosh Baheti, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 0 days.

(21) Appl. No.: 15/891,086

(22) Filed: Feb. 7, 2018

(51) Int. Cl.
*A61B 5/00* (2006.01)
*A61B 5/16* (2006.01)
*G01S 7/41* (2006.01)
*G06K 9/00* (2006.01)
*G01S 13/89* (2006.01)
*H04N 21/442* (2011.01)

(52) U.S. Cl.
CPC .............. *G01S 13/89* (2013.01); *A61B 5/165* (2013.01); *G01S 7/411* (2013.01); *G06K 9/00302* (2013.01); *H04N 21/44218* (2013.01); *A61B 5/00* (2013.01); *G06K 9/00335* (2013.01)

(58) Field of Classification Search
None
See application file for complete search history.

(56) References Cited

U.S. PATENT DOCUMENTS

| 9,414,786 | B1* | 8/2016 | Brockway | A61B 5/7203 |
| 2008/0222670 | A1* | 9/2008 | Lee | G09B 7/02 |
| | | | | 725/10 |
| 2016/0050031 | A1* | 2/2016 | Hwang | H04B 1/525 |
| | | | | 375/219 |
| 2017/0091637 | A1* | 3/2017 | Chae | G06N 5/048 |
| 2017/0238859 | A1* | 8/2017 | Sadowsky | G06F 19/00 |
| 2018/0275272 | A1* | 9/2018 | Questa | G01S 15/8959 |

OTHER PUBLICATIONS

Birsan et al., "Time-Frequency Analysis in Doppler Radar for Noncontact Cardiopulmonary Monitoring", Proceeding of 3rd International Conference on EHB, 2011 (Year: 2011).*
Droitcour et al., "A Microwave Radio for Doppler Radar Sensing of Vital Signs", MTT-S Digest, IEEE, 2001 (Year: 2001).*
Tariq, "Vital Signs Monitoring using Doppler Radar and On-Body Antennas"; University of Birmingham, Aug. 2012 (Year: 2012).*

(Continued)

*Primary Examiner* — James R Marandi
(74) *Attorney, Agent, or Firm* — Slater Matsil, LLP

(57) ABSTRACT

An embodiment method may include receiving radar data at a millimeter-wave radar sensor, the radar data being generated in response to an incident radio-frequency signal reflecting off a biological target located in a field of view of the millimeter-wave radar sensor; extracting a filtered vital-Doppler signal from the radar data; determining an emotion of the biological target based on the filtered vital-Doppler signal; and generating a user-engagement rating indicative of a level of engagement of the biological target in an activity performed in the field of view based on the emotion.

17 Claims, 20 Drawing Sheets

(56) References Cited

OTHER PUBLICATIONS

Filippelli, Mario et al., "Respiratory dynamics during laughter," J Appl Physiol, (90), Apr. 2001, http://jap.physiology.org/content/jap/90/4/1441.full.pdf, pp. 1441-1446.

Gu, Changzhan et al., "Assessment of Human Respiration Patterns via Noncontact Sensing Using Doppler Multi-Radar System," Sensors Mar. 2015, 15(3), 6383-6398, doi: 10.3390/s150306383, 17 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, pp. 18-34.

\* cited by examiner

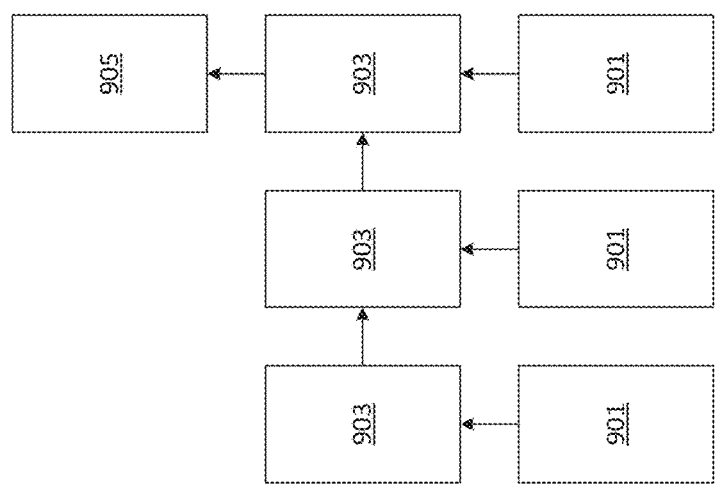

US 10,310,073 B1

SYSTEM AND METHOD FOR DETERMINING ENGAGEMENT LEVEL OF A HUMAN BEING USING A MILLIMETER-WAVE RADAR SENSOR

TECHNICAL FIELD

The present invention relates generally to electronic systems, and, in particular embodiments, to a system and method for determining an engagement level of a human being using a millimeter-wave radar sensor.

BACKGROUND

Applications in the millimeter-wave frequency regime have gained significant interest in the past few years due to the rapid advancement in low cost semiconductor technologies such as silicon germanium (SiGe) and fine geometry complementary metal-oxide semiconductor (CMOS) processes. Availability of high-speed bipolar and metal-oxide semiconductor (MOS) transistors has led to a growing demand for integrated circuits for millimeter-wave applications at 60 GHz, 77 GHz, and 80 GHz and also beyond 100 GHz. Such applications include, for example, automotive radar systems and multi-gigabit communication systems.

In some radar systems, the distance between the radar and a target is determined by transmitting a frequency modulated signal, receiving a reflection of the frequency modulated signal, and determining a distance based on a time delay and/or frequency difference between the transmission and reception of the frequency modulated signal. Accordingly, some radar systems include a transmit antenna to transmit the RF signal, a receive antenna to receive the RF, as well as the associated RF circuitry used to generate the transmitted signal and to receive the RF signal. In some cases, multiple antennas may be used to implement directional beams using phased array techniques. A MIMO configuration with multiple chipsets can be used to perform coherent and non-coherent signal processing, as well.

RF signals received by a radar system may be processed to determine a variety of parameters, examples of which include determining the heart rate and/or respiration of human beings within an area. The heart rate and/or respiration of human beings may be indicative of human mood or emotion, and thus, the heart rate and/or respiration may be used as an indicator of user engagement.

SUMMARY

An embodiment method may include receiving radar data at a millimeter-wave radar sensor, the radar data being generated in response to an incident radio-frequency signal reflecting off a biological target located in a field of view of the millimeter-wave radar sensor; extracting a filtered vital-Doppler signal from the radar data; determining an emotion of the biological target based on the filtered vital-Doppler signal; and generating a user-engagement rating indicative of a level of engagement of the biological target in an activity performed in the field of view based on the emotion.

BRIEF DESCRIPTION OF THE DRAWINGS

For a more complete understanding of the present invention, and the advantages thereof, reference is now made to the following descriptions taken in conjunction with the accompanying drawings, in which:

FIG. 9C shows architecture of the recurrent neural network used in the embodiment of FIG. 9A;

Figure 1A:
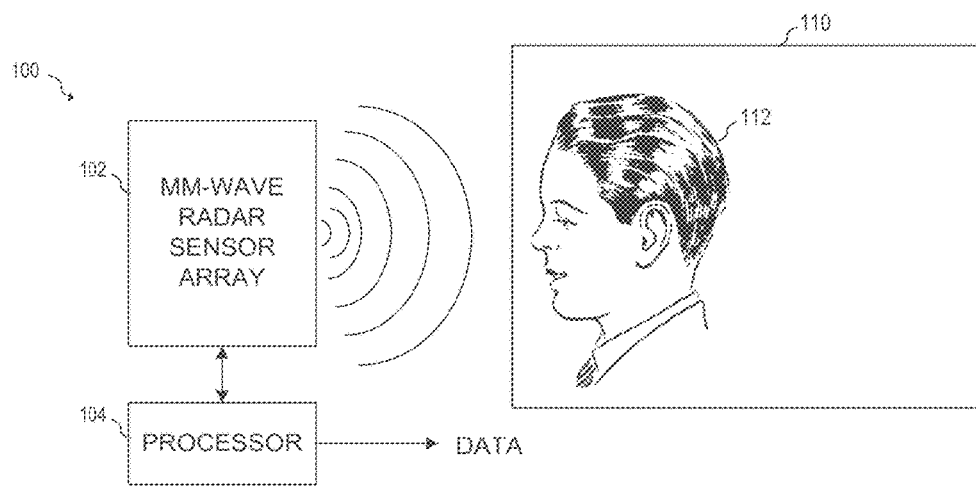
FIG. 1A illustrates an embodiment radar-based detection system.

Corresponding numerals and symbols in different figures generally refer to corresponding parts unless otherwise indicated. The figures are drawn to clearly illustrate the relevant aspects of the preferred embodiments and are not necessarily drawn to scale. To more clearly illustrate certain embodiments, a letter indicating variations of the same structure, material, or process step may follow a figure number.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments. The present disclosure presents a system and method for determining a human being's level of engagement in a particular activity. Examples of activities that a human being may be engaged in include: viewing a movie, a play, or a television episode; listening to music; or playing a video game (e.g. an augmented reality or virtual reality video game). The determination of the human being's level of engagement in such activity may, in turn, be used to generate (e.g. automatically generate) a review or rating of the activity. Such a review or rating may be used by entities to enhance the human being's overall experience when he or she is engaged in such activity. In embodiments described herein, a human being's level of engagement in a particular activity may be determined based on the human being's heart rate and/or respiration, since respiration motion and heart rate are variable and can change in correspondence to different physical and/or emotional states, such as speaking, singing, fear, or stress. For example, a human being's respiration motion (e.g. at the human being's chest or abdomen) may exhibit short inspiration periods followed by long expiration periods when the human being is speaking. As another example, a human being's respiration may be short and rapid when the human being is fearful. Furthermore, when the human being is feeling stressed or anxious, the respiration rate tends to increase and respiration motion shifts from diaphragmatic breathing to chest breathing (e.g. in order to inhale extra oxygen). Additionally, the heart rate and respiratory rate of a human being (and its associated modulation) changes when the human being is feeling scared. As a further example, the heart rate and respiratory rate of a human being also changes and has a specific modulation pattern when the human being is laughing. Based on such observations of the variation of respiration motion and heart rate with different physical and/or emotional states, the system and method proposed in the various embodiments disclosed herein provide a millimeter-wave radar based solution for non-intrusive determination of a human being's level of engagement in a particular activity and for non-intrusive review based on the human being's heart rate and/or respiration. The embodiments disclosed herein are advantageous over current solutions (e.g. electrocardiogram monitors and/or wearable systems) in that the embodiments do not cause discomfort to the human being, are accurate in measuring or determining respiration, and allow the human being to breathe normally or spontaneously (thereby allowing for accurate assessment of heart rate, respiration, and level of engagement).

FIG. 1A illustrates a block diagram of a radar-based detection system 100, in accordance with an embodiment. As shown in FIG. 1A, radar-based detection system 100 includes a millimeter-wave radar sensor 102 and a processor 104 that controls the operation of millimeter-wave radar sensor 102. The processor 104 performs various radar signal processing operations on the data produced by millimeter-wave radar sensor 102. During operation, millimeter-wave radar sensor 102 transmits millimeter-wave RF signals that are reflected by a target 112 (e.g. a human being) that is present within an area 110. The area 110 represents any finite area within the field-of-view of the millimeter-wave radar sensor 102 and may represent, for example, a theatre or cinema seat, a living room, an area in front of a computer monitor or game console, or any other physical area in which the presence of objects may be detected by the millimeter-wave radar sensor 102. Further examples of the area 110 within the field-of-view of the millimeter-wave radar sensor 102 are discussed below in reference to FIGS. 3A to 3D.

Millimeter-wave RF signals reflected by the target 112 are received by the millimeter-wave radar sensor 102. The received RF signals are converted to intermediate frequency (IF) signals and the IF signals are converted to a digital representation, for example, by an analog-to-digital converter included in the millimeter-wave radar sensor 102 or coupled between the millimeter-wave radar sensor 102 and the processor 104. The digital representation of the received RF signals may be processed by the processor 104 to produce various data (represented in FIG. 1A by signal DATA). The data may be used for at least one of the following purposes: (1) determining the heart rate and/or respiration of the target 112 within the area 110; (2) determining a level of engagement of the target 112 in an activity performed within the area 110 based on the heart rate and/or respiration of the target 112; and (3) generating a review or rating of the activity performed within the area 110 based on the heart rate and/or respiration of the target 112.

In various embodiments, the target 112 is detected and classified using Doppler analysis of the RF signals received by the millimeter-wave radar sensor 102. In some embodiments, vital-Doppler analysis may be used to detect vital signs of the target 112 (e.g. cardiac or respiratory signals of the target 112). In embodiments that utilize a frequency modulated continuous wave (FMCW) radar sensor, the location of the target 112 within the area 110 may be found by taking a range fast Fourier transform (FFT) of the baseband radar signal produced by the millimeter-wave radar sensor 102, and the motion of the target 112 may be determined, for example, by taking a further FFTs to determine a velocity of the target 112 using Doppler analysis techniques known in the art. In embodiments in which the millimeter-wave radar sensor 102 includes a receive antenna array, further FFTs may also be used to determine the azimuth of the target 112 with respect to the millimeter-wave radar sensor 102. In the example illustrated in FIG. 1A and with regards to vital-Doppler techniques, small detected motions are analyzed to determine whether these motions are indicative of small bodily movements or the heart rate and respiration of a human being. During vital-Doppler steps, the millimeter-wave radar sensor 102 makes a series of radar measures that are more specifically directed toward the target 112. For example, in embodiments in which the millimeter-wave radar sensor 102 includes a transmit antenna array, these directed measurements are performed by steering the radar beam produced by the millimeter-wave radar sensor 102 using phase-array radar techniques. Based on these more directed radar measurements made during vital-Doppler steps, the processor 104 determines whether the target 112 experiences small motions consistent with human vital signs such as heart rate and respiration.

Figure 1B:
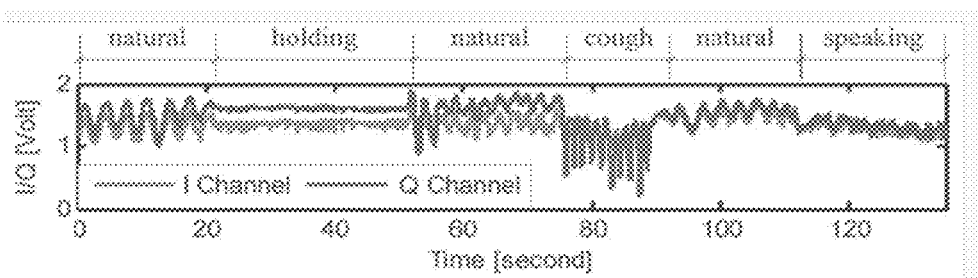
FIGS. 1B to 1G show physical breathing patterns during various human emotional states.
Figure 1C:
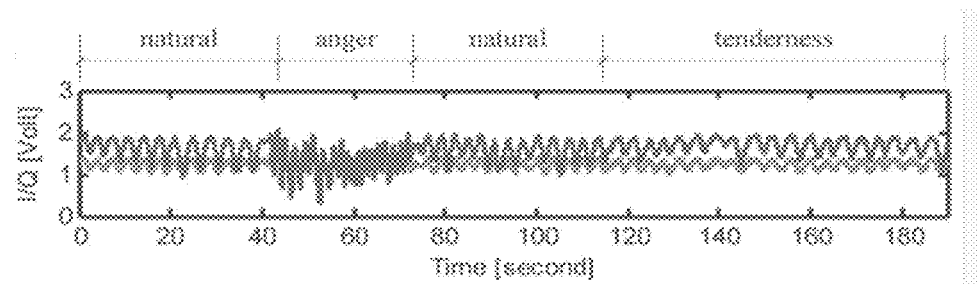
Figure 1D:
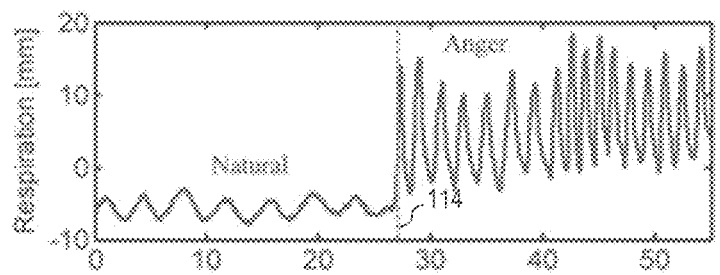
Figure 1E:
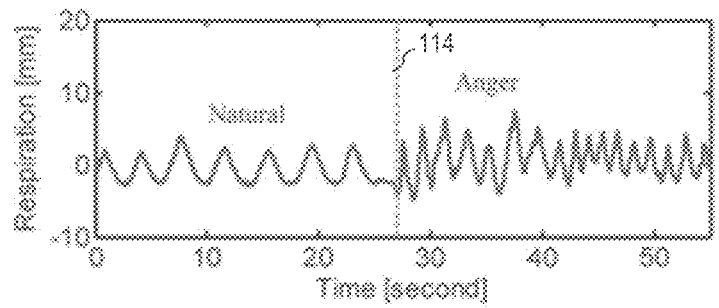
Figure 1F:
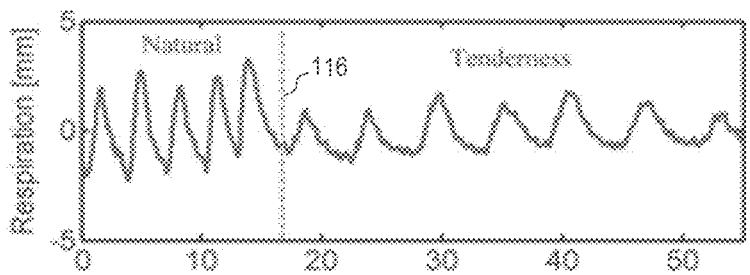
Figure 1G:
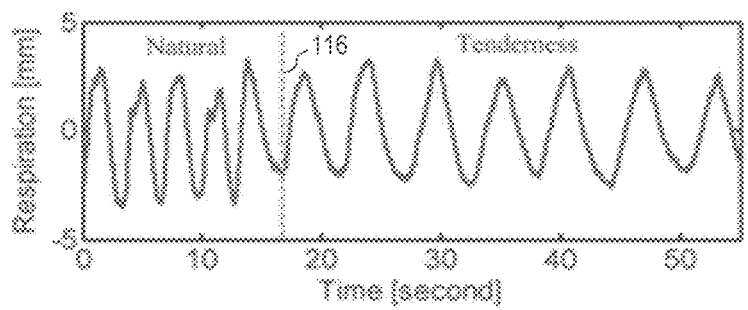

In general, and as discussed above, vital signs may be indicative of human mood and/or emotion. Consequently, vital-Doppler processing of radar data may be used to determine how much (e.g., a level at which) the target 112 is engaged in a particular activity, examples of such activities including, but not limited to, viewing a movie, a play, or a television episode, listening to music, or playing a video game (e.g. an augmented reality or virtual reality video game). FIGS. 1B to 1G show how physical breathing patterns vary with human activity and/or emotion, in accordance with various examples. FIG. 1B shows physical breathing patterns during various human activities such as when a human being is breathing naturally, holding his or her breath, coughing, and speaking. FIG. 1C shows physical breathing patterns during various human emotional states such as when a human being is angry or relaxed (e.g. where the relaxed state is indicated in FIG. 1C as a period of "tenderness"). FIG. 1D shows radar-measured respiration patterns at a human chest during a natural human emotion state and when the human being is angry. FIG. 1E shows radar-measured respiration patterns at a human abdomen during a natural human emotion state and when the human being is angry. The dashed line 114 indicates the transition from natural breathing to the emotional state of "anger." FIGS. 1F and 1G shows radar-measured respiration patterns at a human chest and at a human abdomen, respectively, during a natural human emotion state and when the human being is relaxed (e.g. where the relaxed state is indicated in FIGS. 1F and 1G as a period of "tenderness"). The dashed line 116 indicates the transition from natural breathing to the emotional state of "tenderness."

Figure 2A:
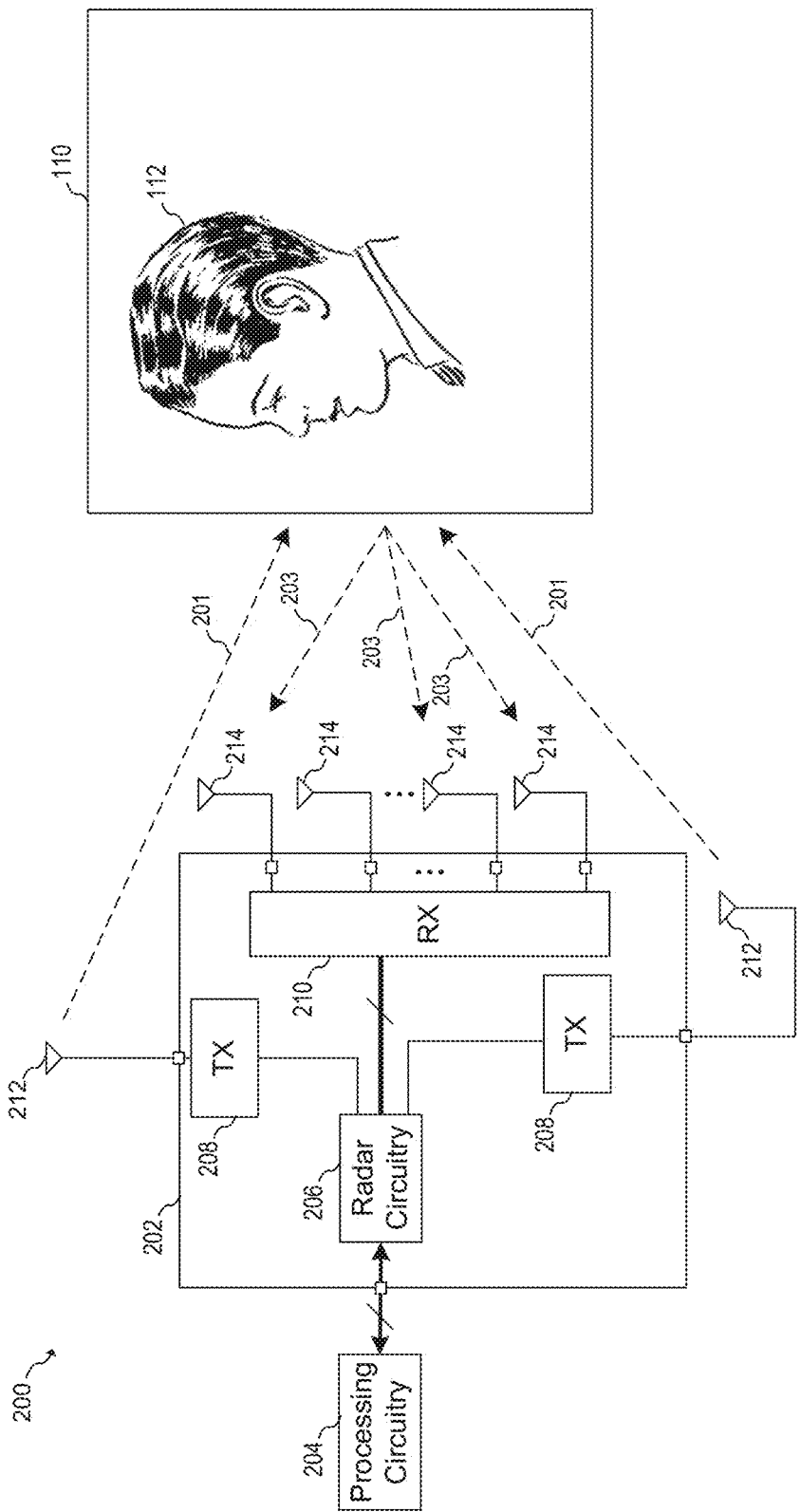
FIG. 2A illustrates a block diagram of an embodiment millimeter-wave radar sensor.

FIG. 2A illustrates a block diagram of a millimeter-wave radar sensor system 200 that may be used to implement millimeter-wave radar sensor circuits in the various disclosed embodiments. Millimeter-wave radar sensor system 200 includes a millimeter-wave radar sensor circuit 202 and processing circuitry 204. Embodiment millimeter-wave radar sensor circuits may be implemented, for example, using a two-dimensional millimeter-wave phase-array radar that measures the position and relative speed of the target 112. The millimeter-wave phase-array radar transmits and receives signals in the 20 GHz to 122 GHz range (e.g. a frequency range of 57 GHz to 64 GHz for 7 GHz bandwidth). Alternatively, frequencies outside of this range may also be used. For example, different frequency ranges and bandwidths could be used, as the resolution of the system generally is proportional to the bandwidth. In some embodiments, the millimeter-wave radar sensor circuit 202 operates as a frequency modulated continuous wave (FMCW) radar sensor having multiple transmit and receive channels. Alternatively, other types of radar systems may be used such as pulse radar, Monte Carlo forecasting of waves (MCFW), and non-linear frequency modulation (NLFM) to implement millimeter-wave radar sensor circuit 202.

The millimeter-wave radar sensor circuit 202 transmits and receives radio signals for detecting the presence and motion of the target 112 in three-dimensional space. For example, the millimeter-wave radar sensor circuit 202 transmits an incident RF signals 201 and receives RF signals 203 that are reflection of the incident RF signals from the target 112. The received reflected RF signals 203 are down-converted by the millimeter-wave radar sensor circuit 202 to determine beat frequency signals. These beat frequency signals may be used to determine information such as the location, speed, angle, etc., of the target 112 in three-dimensional space.

In various embodiments, the millimeter-wave radar sensor circuit 202 is configured to transmit incident RF signals 201 toward the target 112 via transmit antennas 212 and to receive reflected RF signals 203 from the target 112 via receive antennas 214. The millimeter-wave radar sensor circuit 202 includes transmitter front-end circuits 208 coupled to transmit antennas 212 and receiver front-end circuit 210 coupled to receive antennas 214.

During operation, transmitter front-end circuits 208 may transmit RF signals toward the target 112 simultaneously or individually using beamforming depending on the phase of operation. While two transmitter front-end circuits 208 are depicted in FIG. 2A, it should be appreciated that millimeter-wave radar sensor circuit 202 may include greater than two transmitter front-end circuits 208. Thus, in various embodiments, the number of transmitters can be extended to n×m. Each transmitter front-end circuit 208 includes circuitry configured to produce the incident RF signals. Such circuitry may include, for example, RF oscillators, up-converting mixers, RF amplifiers, variable gain amplifiers, filters, transformers, power splitters, and other types of circuits.

Receiver front-end circuit 210 receives and processes the reflected RF signals from the target 112. As shown in FIG. 2A, receiver front-end circuit 210 is configured to be coupled to four receive antennas 214, which may be configured, for example, as a 2×2 antenna array. In alternative embodiments, receiver front-end circuit 210 may be configured to be coupled to greater or fewer than four antennas, with the resulting antenna array being of various n×m dimensions depending on the specific embodiment and its specifications. Receiver front-end circuit 210 may include, for example, RF oscillators, up-converting mixers, RF amplifiers, variable gain amplifiers, filters, transformers, power combiners and other types of circuits.

Radar circuitry 206 provides signals to be transmitted to transmitter front-end circuits 208, receives signals from receiver front-end circuit 210, and may be configured to control the operation of millimeter-wave radar sensor circuit 202. In some embodiments, radar circuitry 206 includes, but is not limited to, frequency synthesis circuitry, up-conversion and down-conversion circuitry, variable gain amplifiers, analog-to-digital converters, digital-to-analog converters, digital signal processing circuitry for baseband signals, bias generation circuits, and voltage regulators.

Radar circuitry 206 may receive a baseband radar signal from processing circuitry 204 and control a frequency of an RF oscillator based on the received baseband signal. In some embodiments, this received baseband signal may represent a FMCW frequency chirp to be transmitted. Radar circuitry 206 may adjust the frequency of the RF oscillator by applying a signal proportional to the received baseband signal to a frequency control input of a phase locked loop. Alternatively, the baseband signal received from processing circuitry 204 may be up-converted using one or more mixers. Radar circuitry 206 may transmit and digitize baseband signals via a digital bus (e.g., a USB bus), transmit and receive analog signals via an analog signal path, and/or transmit and/or receive a combination of analog and digital signals to and from processing circuitry 204.

Processing circuitry 204 acquires baseband signals provided by radar circuitry 206 and formats the acquired baseband signals for transmission to an embodiment signal processing unit. These acquired baseband signals may represent beat frequencies, for example. In some embodiments, processing circuitry 204 includes a bus interface (not shown) for transferring data to other components within the radar-based detection system. Optionally, processing circuitry 204 may also perform signal processing steps used by embodiment detection systems such as an FFT, a short-time Fourier transform (STFT), vital-Doppler analysis, object classification, machine learning, and the like. In addition to processing the acquired baseband signals, processing circuitry 204 may also control aspects of millimeter-wave radar sensor circuit 202, such as controlling the transmissions produced by millimeter-wave radar sensor circuit 202.

The various components of millimeter-wave radar sensor system 200 may be partitioned in various ways. For example, millimeter-wave radar sensor circuit 202 may be implemented on one or more RF integrated circuits (RFICs), antennas 212 and 214 may be disposed on a circuit board, and processing circuitry 204 may be implemented using a processor, a microprocessor, a digital signal processor and/or a custom logic circuit disposed on one or more integrated circuits/semiconductor substrates. Processing circuitry 204 may include a processor that executes instructions in an executable program stored in a non-transitory computer readable storage medium, such as a memory to perform the functions of processing circuitry 204. In some embodiments, however, all or part of the functionality of processing circuitry 204 may be incorporated on the same integrated circuit/semiconductor substrate on which millimeter-wave radar sensor circuit 202 is disposed.

In some embodiments, some or all portions of millimeter-wave radar sensor circuit 202 may be implemented in a package that contains transmit antennas 212, receive antennas 214, transmitter front-end circuits 208, receiver front-end circuit 210, and/or radar circuitry 206. In some embodiments, millimeter-wave radar sensor circuit 202 may be implemented as one or more integrated circuits disposed on a circuit board, and transmit antennas 212 and receive antennas 214 may be implemented on the circuit board adjacent to the integrated circuits. In some embodiments, transmitter front-end circuits 208, receiver front-end circuit 210, and radar circuitry 206 are formed on a same radar front-end integrated circuit (IC) die. Transmit antennas 212 and receive antennas 214 may be part of the radar front-end IC die, or may be implemented as separate antennas disposed over or adjacent to the radar front-end IC die. The radar front-end IC die may further include conductive layers, such as redistribution layers (RDLs), used for routing and/or for the implementation of various passive or active devices of millimeter-wave radar sensor circuit 202. In an embodiment, transmit antennas 212 and receive antennas 214 may be implemented using the RDLs of the radar front-end IC die.

Figure 2B:
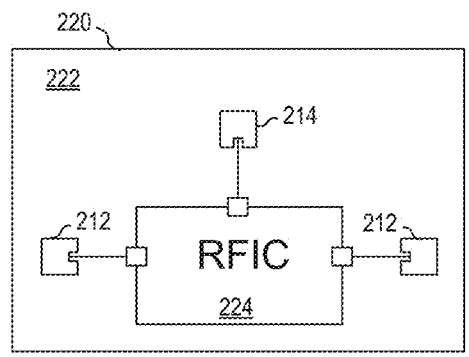
FIGS. 2B and 2C illustrate plan views of embodiment millimeter-wave radar sensor circuits.

FIG. 2B illustrates a plan view of millimeter-wave radar sensor circuit 220 that may be used to implement millimeter-wave radar sensor circuit 202. As shown, millimeter-wave radar sensor circuit 220 is implemented as an RFIC 224 coupled to transmit antennas 212 and receive antenna 214 implemented as patch antennas disposed on or within substrate 222. In some embodiments, substrate 222 may be implemented using a circuit board on which millimeter-wave radar sensor circuit 202 is disposed and on which transmit antennas 212 and receive antennas 214 are implemented using conductive layers of the circuit board. Alternatively, substrate 222 represents a wafer substrate on which one or more RDLs are disposed and on which transmit antennas 212 and receive antennas 214 are implemented using conductive layers on the one or more RDLs.

Figure 2C:
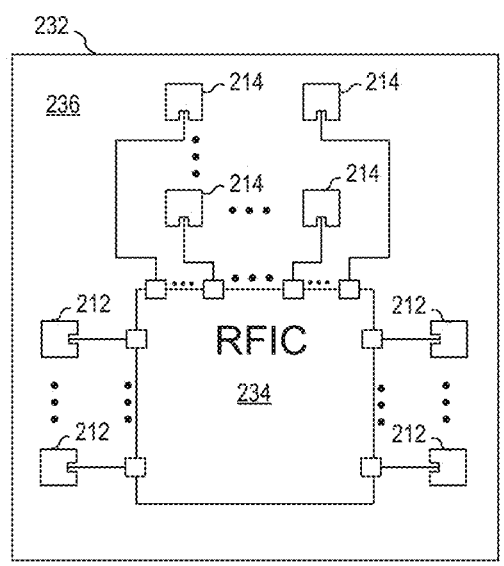

FIG. 2C illustrates a plan view of millimeter-wave radar sensor circuit 232 that includes an array of transmit antennas 212 and an array of receive antennas 214 coupled to RFIC 234 disposed on substrate 236. In various embodiments, transmit antennas 212 may form an array of m antennas and receive antennas 214 may form an array of n antennas. Each of the m transmit antennas 212 are coupled to a corresponding pin on RFIC 234 and coupled to a corresponding transmit circuit within RFIC 234; and each of the n receive antennas 214 are coupled to a corresponding pin on RFIC 234 and coupled to a corresponding receive circuit within RFIC 234. In various embodiments, the array of transmit antennas 212 and the array of receive antennas 214 may be implemented as a uniform array or a linear array of any dimension. It should be appreciated that the implementations of FIGS. 2B and 2C are just two examples of the many ways that embodiment millimeter-wave radar sensor circuits could be implemented.

Figure 3A:
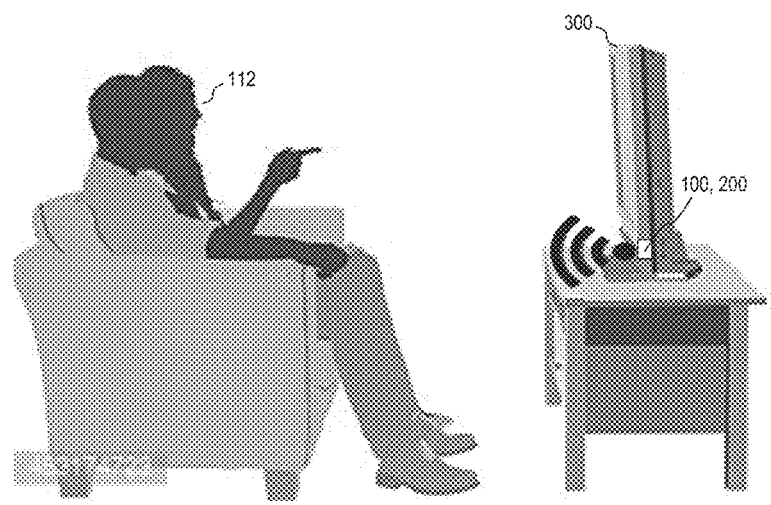
FIGS. 3A to 3D show various examples of objects that may include the millimeter-wave radar sensor system of FIG. 1A or FIGS. 2A-2C.

FIGS. 3A to 3D show various examples of objects that may include the millimeter-wave radar sensor system 100 of FIG. 1A or the millimeter-wave radar sensor system 200 of FIGS. 2A-2C. FIG. 3A shows an example where the millimeter-wave radar sensor system 100 or 200 is included in a television or computer screen 300. In the example shown in FIG. 3A, the millimeter-wave radar sensor system 100 or 200 may be configured to extract user data from a field of view of the millimeter-wave radar sensor system 100 or 200. For example, the millimeter-wave radar sensor system 100 or 200 may be configured to determine at least one of the number and/or location of the targets 112 or the breathing and/or respiration patterns of the targets 112. In some embodiments, the television or computer screen 300 may be connected to a network (e.g. a cloud network), thereby allowing the television or computer screen 300 to have access to information regarding a program or episode that the targets 112 are viewing. Access to such information allows the television or computer screen 300 to provide feedback (e.g. to the cloud network) on how the targets 112 responded to the program or episode based on motion, respiration, heart rate, and/or position of the targets 112 during screening of the program or episode on the television or computer screen 300.

Figure 3B:
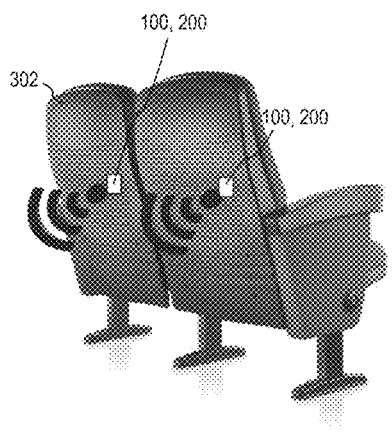
Figure 3C:
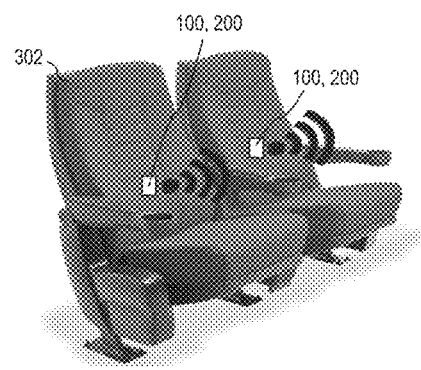

FIGS. 3B and 3C show examples where the millimeter-wave radar sensor system 100 or 200 is included in a theatre or cinema seat 302. In the example shown in FIGS. 3B and 3C, the millimeter-wave radar sensor system 100 or 200 may be configured to extract data from a field of view of the millimeter-wave radar sensor system 100 or 200. In the example of FIG. 3B, the millimeter-wave radar sensor system 100 or 200 may be configured to extract data from an area behind the seat 302, while in the example of FIG. 3C, the millimeter-wave radar sensor system 100 or 200 may be configured to extract data from an area in or in front of the seat 302. In some embodiments, the millimeter-wave radar sensor system 100 or 200 of FIGS. 3B and 3C may be configured to determine human motion and/or extract vital signature (e.g. heart rate and/or respiration signature) of the target 112. Additionally or alternatively, the millimeter-wave radar sensor system 100 or 200 may be configured to generate human behavior patterns and classify such patterns. Furthermore, the millimeter-wave radar sensor system 100 or 200 may be configured to enhance real-time three-dimensional (3D) immersive sound experience by adapting sound played through speakers included within or mounted on the seat 302.

Figure 3D:
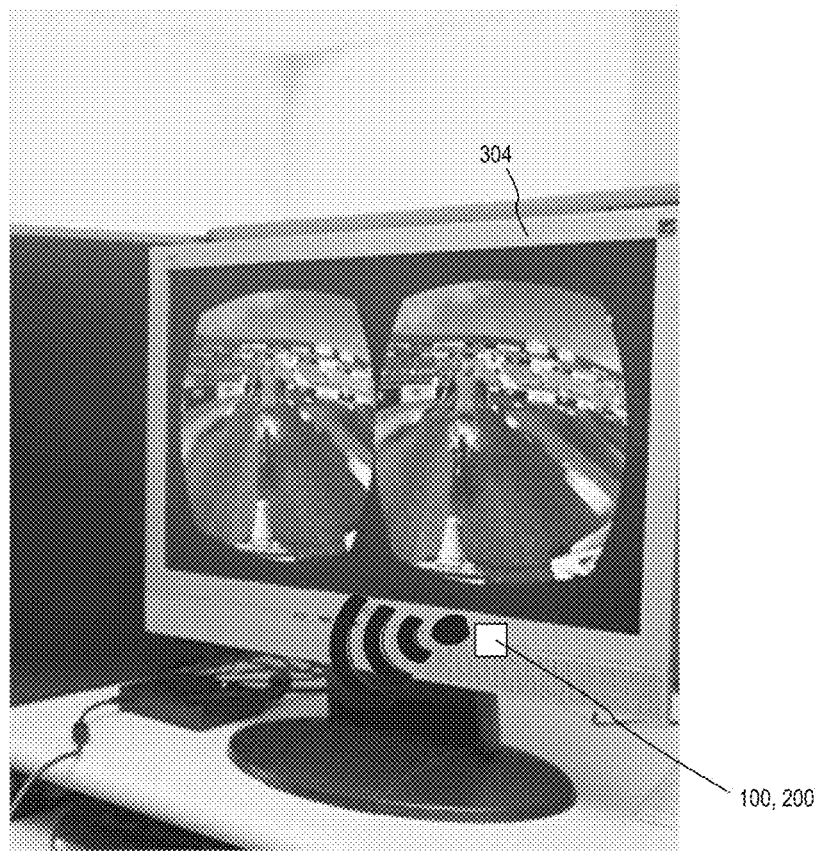

FIG. 3D shows an example where the millimeter-wave radar sensor system 100 or 200 is included in a gaming (e.g. virtual reality) console 304. In the example shown in FIG. 3D, the millimeter-wave radar sensor system 100 or 200 may be configured to extract data from a field of view of the millimeter-wave radar sensor system 100 or 200. In some embodiments, the millimeter-wave radar sensor system 100 or 200 may be configured to determine human motion and/or extract vital signature (e.g. heart rate and/or respiration signature) of the target 112. Additionally or alternatively, the millimeter-wave radar sensor system 100 or 200 may be configured to generate human behavior patterns and classify such patterns. Furthermore, the millimeter-wave radar sensor system 100 or 200 may be configured to generate (e.g. automatically generate) a review of the gaming experience based on heart rate, respiration, and/or motion determined by the millimeter-wave radar sensor system 100 or 200.

Furthermore, the millimeter-wave radar sensor system 100 or 200 may be configured to adapt video or audio effects and/or feedback based on heart rate, respiration, and/or motion determined by the millimeter-wave radar sensor system 100 or 200.

Figure 4A:
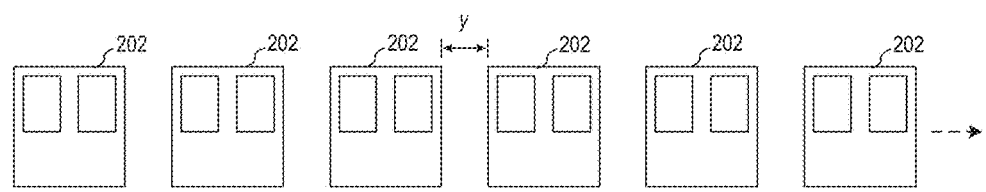
FIGS. 4A-4D illustrate various configurations for the placement of millimeter-wave radar sensors within the objects shown in FIGS. 3A to 3D.
Figure 4B:
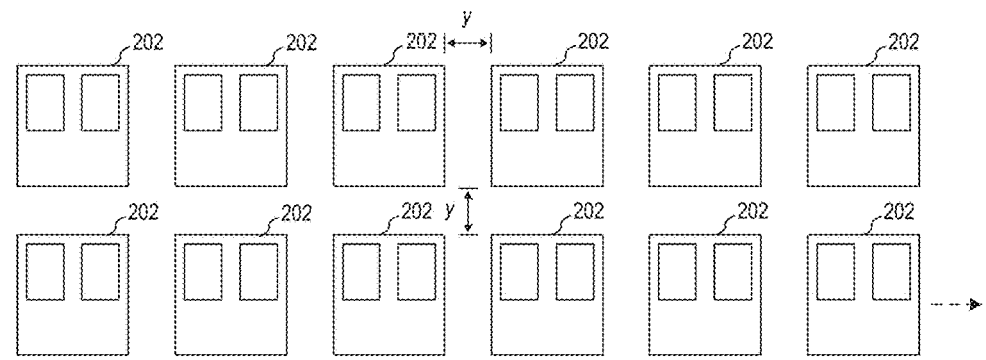
Figure 4C:
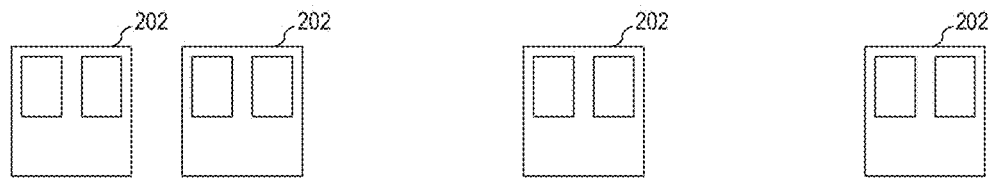
Figure 4D:
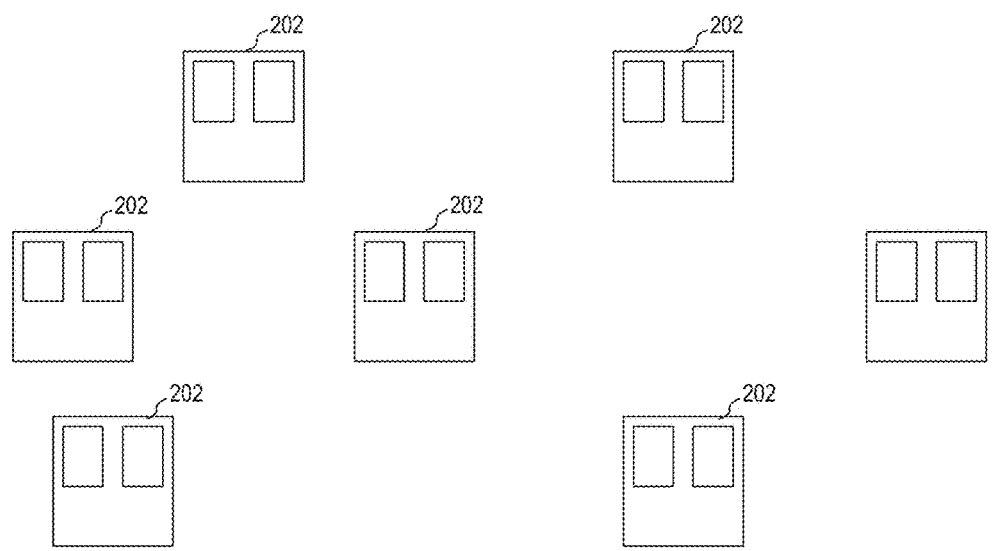

FIGS. 4A-4D illustrate various configurations for the placement of millimeter-wave radar sensors 202 within the objects shown in FIGS. 3A to 3D. FIG. 4A illustrates millimeter-wave radar sensors 202 configured in a uniform linear array with a distance y between each sensor. While six millimeter-wave radar sensors 202 are shown in the illustration, it should be understood that greater or fewer than six millimeter-wave radar sensors 202 may be used depending on the specific embodiment and its specifications. FIG. 4B illustrates millimeter-wave radar sensors 202 configured in a uniform rectangular array with a distance y between each sensor. While an array of 2×6 millimeter-wave radar sensors 202 are shown in the illustration, it should be understood that any rectangular array dimension may be used depending on the specific embodiment and its specifications. Configuring millimeter-wave radar sensors 202 in a rectangular configuration helps to improve cross-range resolution. In various embodiments, the range of the radar system is a distance between the sensor 202 and the target 112, while the cross-range of the resolution pertains to a spatial resolution within a sensing place of radar sensors 202. Millimeter-wave radar sensors 202 may also be implemented in a non-uniform configuration. For example, FIG. 4C illustrates millimeter-wave radar sensors 202 configured in a non-uniform linear array, and FIG. 4D illustrates millimeter-wave radar sensors 202 configured in a non-uniform two-dimensional array. In various embodiments, millimeter-wave radar sensors 202 have a minimum distance of between $0.5\lambda$ and $0.7\lambda$ between each other where $\lambda$ is the wavelength of the millimeter-wave RF signal. This distance between millimeter-wave radar sensors 202 may be increased when the position of each sensor is known for processing extracted data.

It is noted that the uniform linear array of FIG. 4A or the non-uniform linear array of FIG. 4C may be useful for embodiments where the millimeter-wave radar sensors 202 are placed within the television screen 300 of FIG. 3A, since scenes on the television screen 300 are typically played to a plurality of human beings 112. Consequently, transmit beamforming may be used to segregate or differentiate among the plurality of human beings 112, thereby allowing extraction of respective data (e.g. respective vital signs) from each of the plurality of human beings 112.

In various embodiments, millimeter-wave radar sensors 202 may be mounted on a variety of surfaces and may be hidden under different materials and/or radome types that include, for example, polycarbonate, glass, plastics and other materials. In some embodiments, metals are not used above the sensor system. In other embodiments, metals may be used above the sensor plane as a shield or a waveguide depending on the particular system. For example, in a yagi antenna disposed on the substrate of millimeter-wave radar sensor 202 may be used to transmit or receive a signal in the same plane as the sensor. In such a case, the antenna may be rotated by 90 degrees such that bean produced by the radar sensor is directed toward the target. A metal shield may be disposed above the antenna. In some cases, the power levels transmitted by millimeter-wave radar sensors 202 may be limited to comply with government regulations, such as regulations promulgated by the United States Federal Communications Commission (FCC). In some embodiments, any uniform linear array (ULA), non-uniform linear array (NULA), uniform rectangular array (URA) or non-uniform rectangular array (NURA) can be used depending on resolution requirements, power consumption, system space available etc.

Figure 5:
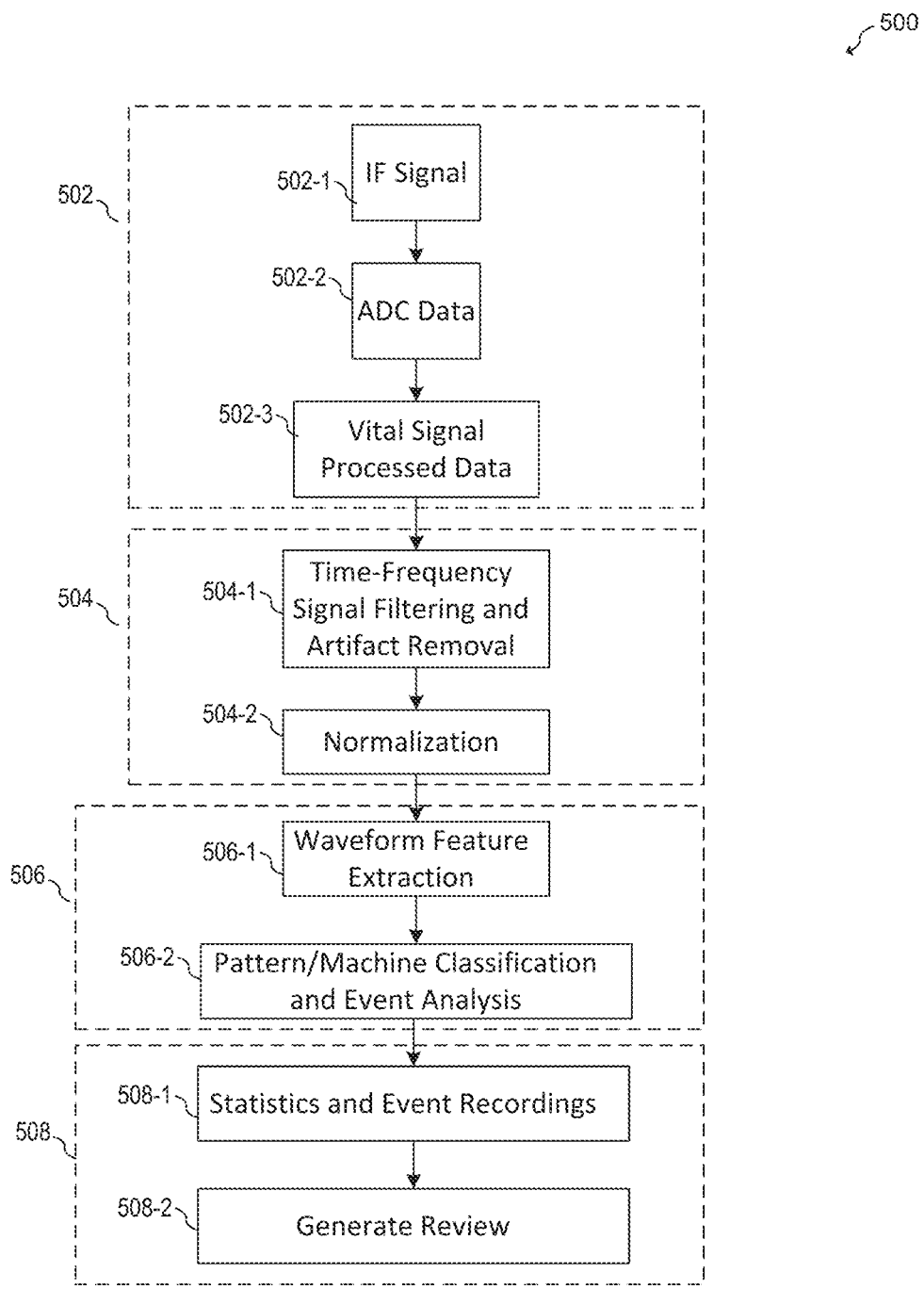
FIG. 5 shows a method of determining a human being's level of engagement in a particular activity and generating a review or rating of the activity, in accordance with an embodiment.

FIG. 5 shows a method 500 of determining a human being's level of engagement in a particular activity and generating a review or rating of the activity, in accordance with an embodiment. In general, the method 500 includes a data acquisition step 502, a data preparation step 504, a prediction step 506, and a review generation step 508. The data acquisition step 502 may include the steps of receiving an IF signal (in step 502-1), converting the IF signal to digital radar data (in step 502-2), and processing the digital radar data to extract time-domain vital signals therefrom (in step 502-3). The data preparation step 504 may generate a clean vital-Doppler signal from the time-domain vital signals generated by the data acquisition step 502. The data preparation step 504 may include the steps of filtering a time-frequency signal (e.g. obtained from the vital-Doppler signals) and removing artifacts from the time-frequency signal (in step 504-1). The data preparation step 504 may further include signal normalization (in step 504-2). The prediction step 506 may include the steps of waveform feature extraction (in step 506-1) and pattern and/or machine classification and event analysis (in step 506-2). Finally, the review generation step 508 may include the steps of statistics and event recording (in step 508-1) and generating a review (in step 508-2). The various steps of the method 500 are described in greater detail in the description that follows.

Figure 6A:
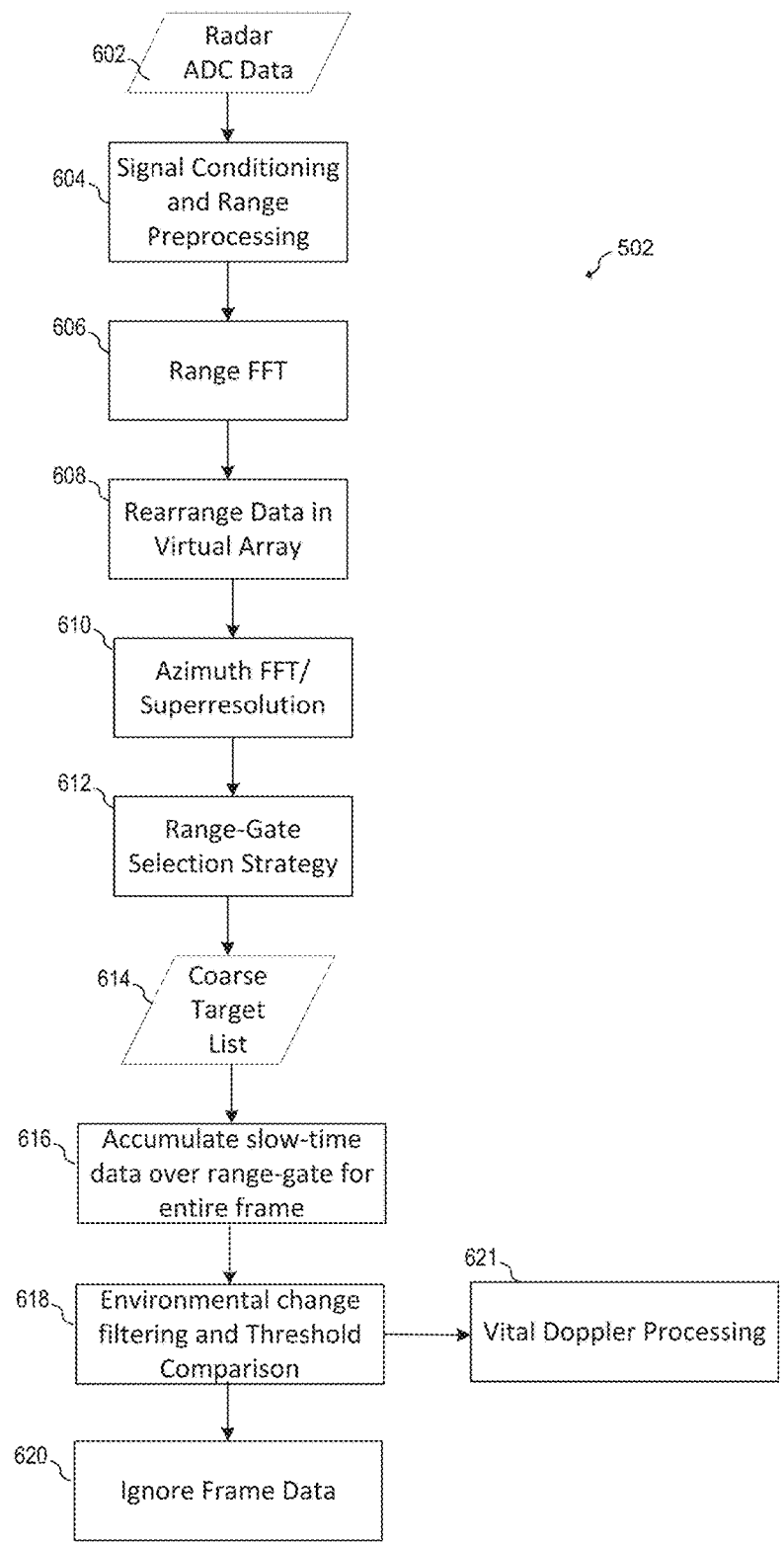
FIG. 6A shows, in greater detail, a data acquisition step of the method shown in FIG. 5, in accordance with an embodiment.

FIG. 6A shows, in greater detail, the data acquisition step 502 of the method 500 shown in FIG. 5 where time-domain vital signals are extracted from digital radar data, in accordance with an embodiment. The data acquisition step 502 includes reception of digital radar data (in step 602) by the millimeter-wave radar sensor. To obtain the digital radar data, a series of chirps is transmitted and subsequently received by a millimeter-wave radar sensor, such as millimeter-wave radar sensors 102, 202, 220 and 232 shown in FIGS. 1A, 2A, 2B and 2C, respectively. These radar measurements, which can include baseband beat frequencies, are digitized and stored as digital radar data. In step 604, signal conditioning and range preprocessing is performed. During step 604, digital radar data is filtered, DC components are removed, and the IF data is cleared. In some embodiments, IF data is cleared by filtering to remove the Tx-Rx self-interference and optionally pre-filtering the interference colored noise. In some embodiments, filtering includes removing data outliers that have significantly different values from other neighboring range-gate measurements. In a specific example, a Hampel filter is applied with a sliding window at each range-gate to remove such outliers. Alternatively, other filtering for range preprocessing known in the art may be used.

In step 606, a range FFT is taken of the filtered radar data produced by step 604. Each point of the range FFT represents a distance between the millimeter-wave sensor and a detected object and corresponds to a range gate. In some embodiments, a range FFT is performed for radar data produced by each receive antenna in a receive antenna array.

In step 608, the data produced by range FFT step 606 is rearranged in a virtual array. Here, multiple receiver data is stitched together for improved angular resolution using methods known in the art. In step 610, an azimuth FFT is performed on the virtual array data produced in step 608 using higher order beamforming and super-resolution techniques known in the art. In various embodiments, the range FFT provides an indication as to the angular location of the detected objects with respect to the position of the millimeter-wave radar sensor. In alternative embodiments, other transform types could be used besides an FFT for the range and azimuth FFTs of steps 606 and 610, such as a Discrete Fourier Transform (DFT) or other transform types such as a z-transform.

In step 612, a range-gate selection strategy is implemented in order to determine which range-gates represent detected objects. In some embodiments, range-gates whose mean is greater than the mean of all the other range gates in its field of view are selected as potential target range-gates. In various embodiments, the range-gate selection strategy also determines the angle or azimuth of detected targets with respect to the millimeter-wave radar sensor as well as their range or distance to the millimeter-wave radar sensor. Once it is determined which range gates represent detected objects, a coarse target list is produced (e.g. in step 614) that includes the range and azimuth of each detected object.

The method shown in FIG. 6A also includes step 616, where slow-time data corresponding to a selected range-gate is captured across an entire vital-Doppler frame. In some embodiment, a vital-Doppler frame boundary is defined as 512 consecutive vital-Doppler chirps, with each vital-Doppler chirp being 32 microseconds in duration and with consecutive vital-Doppler chirps being spaced 19.2 milliseconds apart. In general, the slow-time data captured across an entire vital-Doppler frame represent a data segment of range-gate window measurements. In step 618, environmental change filtering is performed on the vital-Doppler frame. In an embodiment, a threshold-based approach is used to determine whether or not the segment of range-gate window measurements contains large body movement or environmental changes by examining the short-time energy of the moving variance of the range-gate. This variance energy may be empirically calculated in some embodiments. Range-gate measurements that fall below the threshold established by the short-time energy of the moving variance of the range-gate are considered to be representative of static objects, and thus such frame data is ignored (in step 620). On the other hand, range-gate measurements that are above the threshold are considered to be representative of a human target being present in the corresponding range-bin. In some embodiments, previously measured vital measurements of objects that are determined to be moving objects are read off to take into disturbances and possible unreliability of vital data due to large movements. A separate environmental change filtering step may be performed for each vital-Doppler frame.

Range-gate measurements that are above the threshold may be subjected to vital-Doppler processing 621, as shown in FIG. 6A. As discussed above, a vital-Doppler frame boundary may be defined as 512 consecutive vital-Doppler chirps, with each vital-Doppler chirp being 32 microseconds in duration and with consecutive vital-Doppler chirps being spaced 19.2 milliseconds apart. Based on these time durations, the vital-Doppler processing step 621 may be capable of detecting a maximum Doppler frequency of 52.083 Hz with a 0.1017 Hz frequency resolution. It is noted that these time durations are merely exemplary and may be different in other embodiments.

Figure 6B:
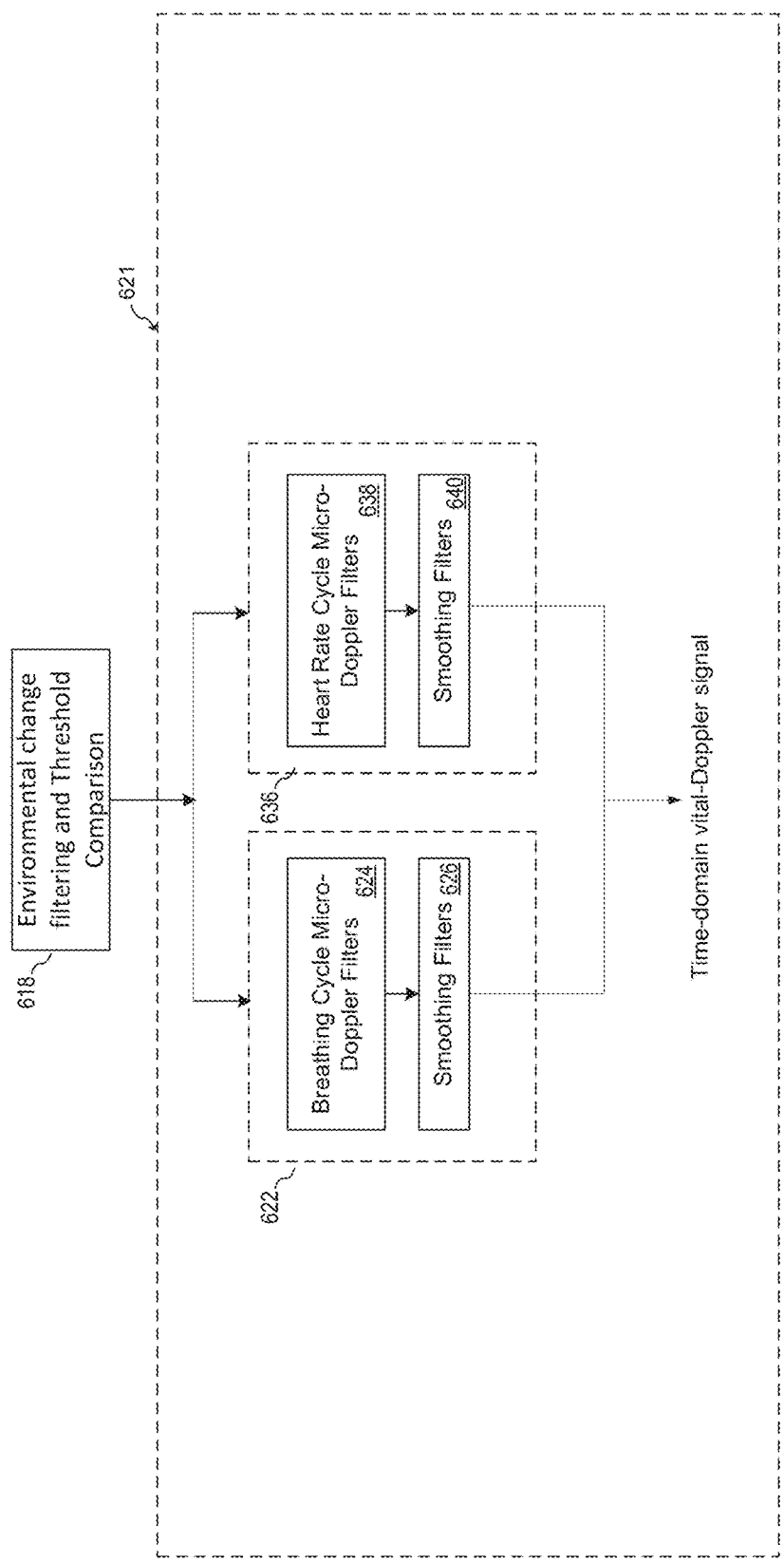
FIG. 6B shows, in greater detail, vital-Doppler processing that is executed on range-gate measurements, in accordance with an embodiment.

FIG. 6B shows the vital-Doppler processing 621 that is executed on range-gate measurements that are above the threshold used in step 618. In the example of FIG. 6B, two fixed, calibrated low bandwidth filters are employed to extract a heart-beat signal and a breathing signal from the range gates selected in step 612. Radar data associated with static inanimate targets such as chairs, TV, etc., produce no vital signals after passing through these filters, whereas radar data associated with human targets produce vital signals after passing through these embodiment filters. Thus, the output of these filters can be used to determine whether or not radar data associated with a detected target corresponds with a human being.

During the respiration vital-Doppler filtering analysis 622, motions corresponding to respiration are extracted from the data in each vital-Doppler frame in steps 624, 626, 628, 630, 632, and 634. In step 624, breathing cycle vital-Doppler filtering is performed. For example, the slow time radar signal from the specific/identified target range gate is fed into a band pass filter to determine the breathing rate. For example, a band-pass filter centered around 0.8 Hz with a bandwidth of 0.6 Hz can be used. The band-pass filter may be implemented by an infinite impulse response (IIR) or finite impulse response (FIR) filter. Alternatively, other center frequencies and bandwidths may be used. In step 626, the output of vital-Doppler filtering step 524 is filtered using, for example, Savitzky-Golay filter to smooth the data, and the output of step 626 may be provided as at least a portion of the time-domain vital Doppler signal.

During the heart rate vital-Doppler filtering analysis 636, motions corresponding to heart rate are extracted from the data in each vital-Doppler frame radar data in steps 638, 640, 642, 644, 646 and 648 in a similar manner as breathing cycle vital-Doppler filtering analysis 622. In step 638, heart rate vital-Doppler filtering is performed. For example, the slow time radar signal from the specific/identified target range gate is fed into a band pass filter to determine the heart rate. For example, a band-pass filter centered around 2 Hz with a bandwidth of 3 Hz can be used. The band-pass filter may be implemented by an infinite impulse response (IIR) or finite impulse response (FIR) filter. Alternatively, other center frequencies and bandwidths may be used. In step 640, the output of vital-Doppler filtering step 638 is filtered using, for example, a low-pass filter to smooth the data, and the output of step 640 may be provided as at least a portion of the time-domain vital Doppler signal.

Figure 7A:
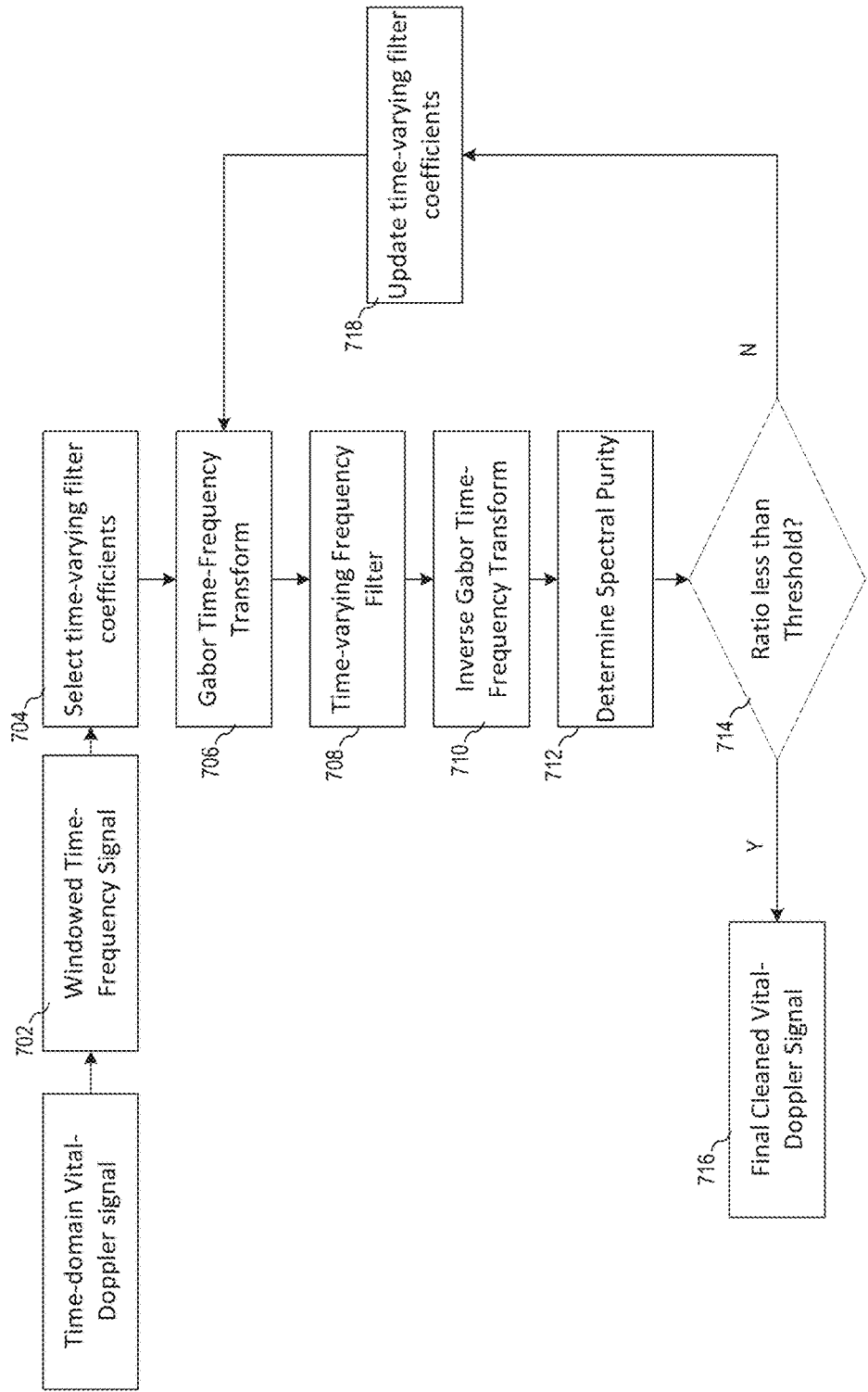
FIGS. 7A and 7B show, in greater detail, a data preparation step of the method shown in FIG. 5, in accordance with various embodiments.

FIG. 7A shows, in greater detail, the data preparation step 504 of the method 500 shown in FIG. 5, where a clean vital-Doppler signal is generated from a time-domain vital-Doppler signal, in accordance with an embodiment where iterative time-frequency filtering is performed. In FIG. 7A, the time-domain vital-Doppler signals obtained from the data acquisition step 502 is processed to obtain a signal that is localized in time and frequency. This is achieved using time-frequency analysis methods such as by using a Gabor transform. The Gabor transform localizes signals in time and frequency and may be used to analyze the time-domain waveform of the vital-Doppler signals. The use of Gabor functions advantageously provides the ability to analyze a time domain signal over a particular period of time. This is to be contrasted with standard Fourier transforms, which analyze a signal over all time (i.e. for an infinite duration) and has a good localization in frequency but no localization in time. Consequently, as shown in FIG. 7A, the data preparation step 504 includes the step of generating a windowed time-frequency signal from the time-domain vital-Doppler signal (in step 702). Step 702 may be accomplished by convolving (in the time-domain), the time-domain vital-Doppler signal with a window function that is localized in time and frequency. Some examples of window functions include rectangular, triangular, Hanning, Hamming, Gaussian, and Blackman windows. Localization in time of the window function may be achieved by translating the window, in time, by a specific time delay, while localization in frequency of the window function may be achieved by multiplying the window with a complex exponential having a specific angular frequency. The windowed time-frequency signal obtained in step 702 is then subjected to the Gabor time-frequency transform (in step 706) in accordance with methods known in the art.

As shown in FIG. 7A, the time-varying filter coefficients to be used in a time-varying frequency filter are selected (in step 704) and the windowed time-frequency signal is then filtered using the time-varying frequency filter (in step 708). The time-varying frequency filters used in step 708 have filter coefficients that is fixed for a given time segment, but such filter coefficients vary across different time segments based on the selection made in step 704. In general, the time-varying frequency filter used in step 708 is configured to remove noise from the windowed time-frequency signal (and consequently from the time-domain vital-Doppler signal). In some embodiments, noise may be regarded as signals that exist outside of the frequency band of about 0.6 Hz to about 5 Hz. Following the filtering in step 708, an inverse Gabor time-frequency transform is performed (in step 710) to obtain a filtered time-domain vital-Doppler signal. As shown in FIG. 7A, a spectral purity of the filtered time-domain vital-Doppler signal is determined (in step 712), for example, by comparing the out-of-band energy of the filtered time-domain vital-Doppler signal to a total energy of the filtered time-domain vital-Doppler signal. As described above, the out-of-band energy may refer to the energy of the filtered time-domain vital-Doppler signal outside of the frequency band of about 0.6 Hz to about 5 Hz. In step 714, the spectral purity is compared against a predetermined threshold (e.g. between 65% and 85%, such as, for example, about 70%). In response to a determination that the ratio of the out-of-band energy of the filtered time-domain vital-Doppler signal to the total energy of the filtered time-domain vital-Doppler signal is less than the threshold (thereby indicating high spectral purity), the output of the inverse-Gabor time-frequency transform in step 710 is taken as the final cleaned time-domain vital-Doppler signal (in step 716). However, in response to a determination that the ratio of the out-of-band energy of the filtered time-domain vital-Doppler signal to the total energy of the filtered time-domain vital-Doppler signal is greater than the threshold (thereby indicating low spectral purity), the time-varying filter coefficients are updated (in step 718) and the steps 706, 708, 710, 712, and 714 are repeated based on the updated time-varying filter coefficients until the desired spectral purity is achieved.

Figure 7B:
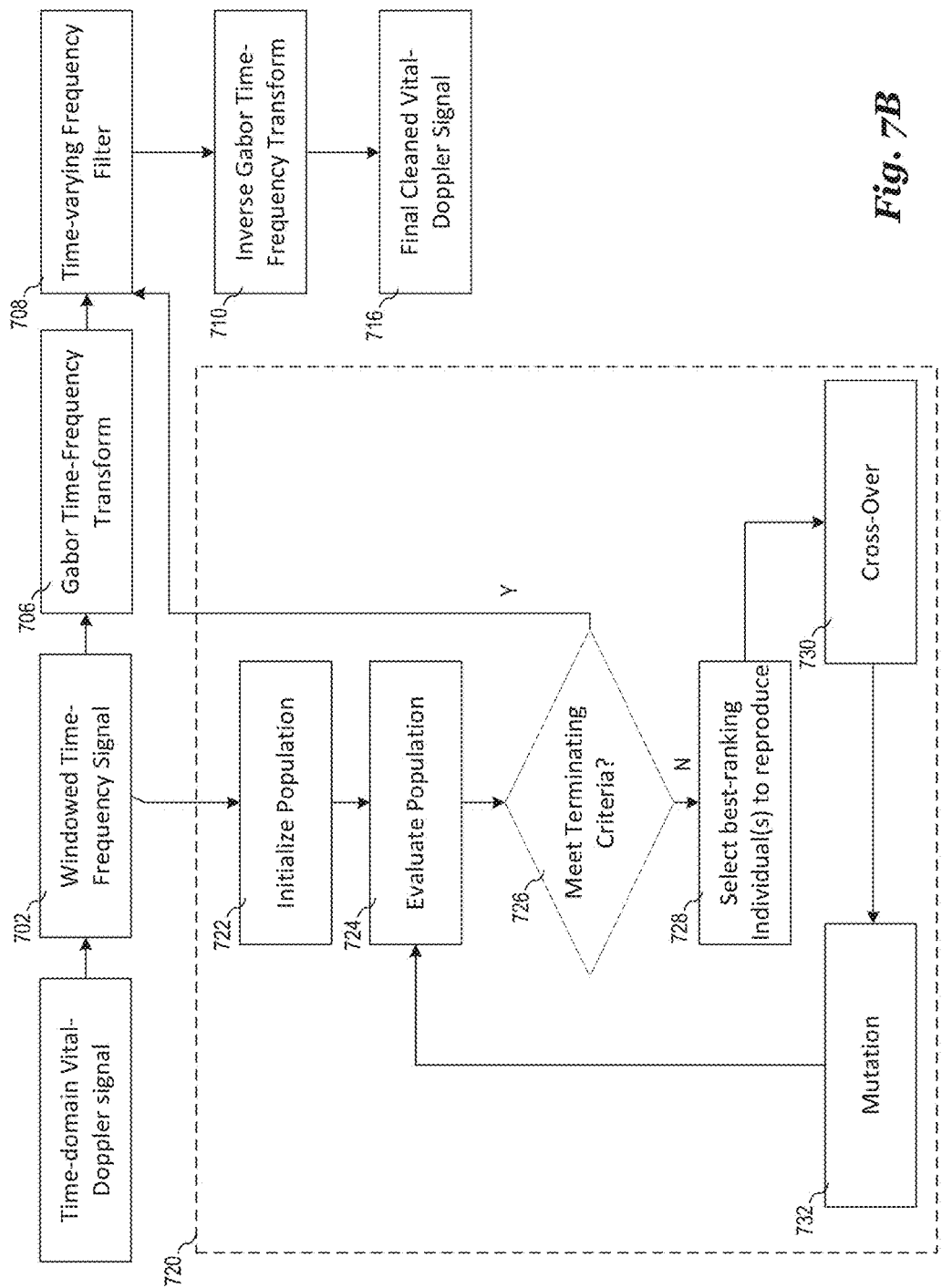

FIG. 7B shows, in greater detail, the data preparation step 504 of the method 500 shown in FIG. 5, where a clean vital-Doppler signal is generated from a time-domain vital-Doppler signal, in accordance with another embodiment where time-frequency filter coefficients are optimized based on a genetic algorithm. It is noted that in the embodiment of FIG. 7A, the time-varying filter coefficients are preselected. However, in the embodiment of FIG. 7B, the time-varying filter coefficients of the time-varying frequency filter used in step 708 are computed on the fly according to the genetic algorithm depicted in FIG. 7B as step 720. In other words, step 720 may be used to compute the time-varying filter coefficients of the time-varying frequency filter used in step 708. In general, the genetic algorithm of step 720 includes the steps of choosing an initial population of individuals (e.g. filter coefficients) (in step 722) and evaluating the fitness of each individual (in step 724). The fitness of each individual is then compared to a terminating criteria (in step 726), and in response to a determination that the terminating criteria has been met, the individuals meeting the terminating criteria are used as the time-varying filter coefficients of the time-varying frequency filter. However, in response to a determination that the terminating criteria are not met, the best-fit or best ranking individuals (e.g. filter coefficients) are selected for reproduction (in step 728). Subsequently, new individuals (e.g. filter coefficients) are bred through cross-over (in step 730) and mutation (in step 732). Subsequently, the fitness of the new individuals are evaluated (in step 724) to determine if the terminating criteria has been met (in 726).

In some embodiments, the step 720 of computing the time-varying filter coefficients on the fly may be accomplished by an expectation-maximization algorithm. In such embodiments, a clustering technique is used to group individuals and to identify their representatives to submit to the user judgment. The other individuals are evaluated according to their similarity to representatives. In expectation-maximization clustering, the algorithm iteratively refines an initial cluster model to fit the data and determines the probability each element can be associated to a cluster. The algorithm ends when the probabilistic model fits the data. The function used to determine the fit is the log-likelihood of the data given the model. It is noted that expectation-maximization includes two steps until convergence is achieved. In the first step (the expectation step), the expected value of the unknown variables is estimated, given the current parameter estimation. In the second step (the maximization step), the distribution parameters are re-estimated to maximize the likelihood of the data, given the expected estimates of the unknown variables.

Figure 8:
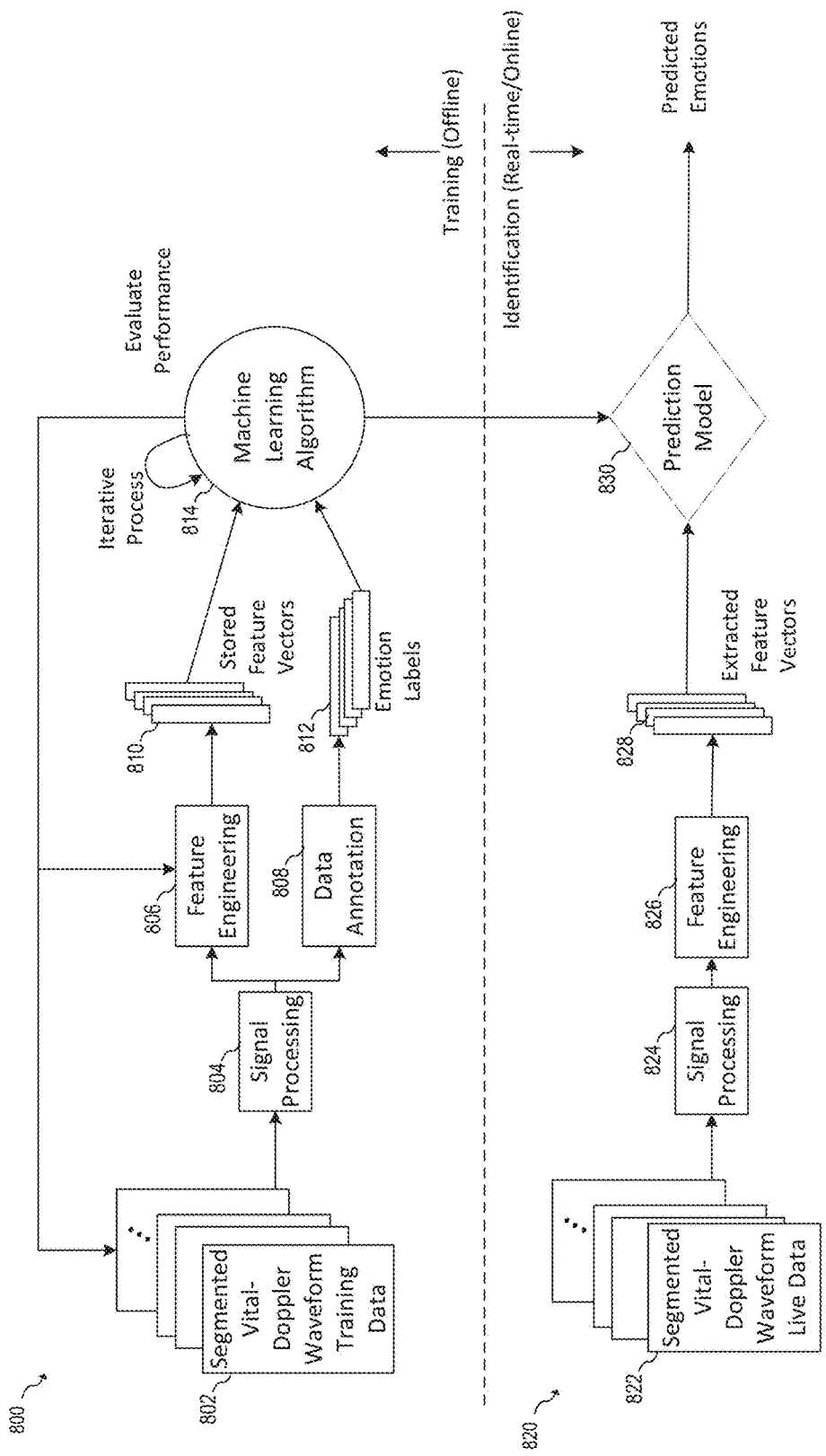
FIG. 8 shows, in greater detail, a prediction step of the method shown in FIG. 5, where a machine learning pipeline, including a training step and an identification step, is used for feature extraction and identification.

FIG. 8 shows, in greater detail, the prediction step 506 of the method 500 shown in FIG. 5, where a machine learning pipeline, including a training step and an identification step, is used for feature extraction and identification. The top portion 800 of FIG. 8 is devoted to the processing storage of features and emotions for comparison to later measurements. The data and steps shown in this portion represent the actions performed when radar measurements are performed and processed for a new user. The bottom portion 820 is devoted to the processing and comparison of new measurements for comparison to stored data. These data and steps represent the actions performed when the system is identifying and validating a user during normal operations.

As shown in the top portion 800 of FIG. 8, segmented vital-Doppler waveform training data 802 (e.g. final cleaned time-domain vital-Doppler signal from step 716) is transformed into stored feature vectors 810 and corresponding emotion labels 812. Training data 802 represents the raw data produced by one or more sets of radar sensor measurements, feature vectors 810 represent sets of generated vectors that are representative of the training data 802, and emotion labels 812 represent user metadata associated with the corresponding training data 802 and feature vectors 810. As shown, training data 802 is transformed into feature vectors 810 (e.g. time-frequency segments) using feature engineering algorithms 806 (e.g. from an azimuth-range map). Signal processing block 804 represents the initial formatting of raw sensor data, and data annotation block 808 represents the derivation of user identification, such as name and official credentials from training data 802. In some embodiments, emotion labels 812 include classes and segregation of user metadata.

During operation, one or more radar images are taken of a user using millimeter-wave sensors described above. In some cases, multiple radar images are recorded to increase the accuracy of identification. Machine learning algorithm 814 evaluates the ability of a prediction model 830 to identify feature vectors and iteratively updates feature engineering algorithm 806 (also referred to as feature extraction block) and training data 802 to increase the classification accuracy of the algorithm. The training performance of the machine learning algorithm may be determined by calculating the cross-entropy performance. In some embodiments, the machine learning algorithm 814 iteratively adjusts feature engineering parameters for a classification accuracy of at least 90%. Alternatively, other classification accuracies could be used.

Machine learning algorithm 814 may be implemented using a variety of machine learning algorithms known in the art. For example, a random forest algorithm or a support vector machine algorithm may be used for classification and analysis of stored feature vectors 810. It is noted that when the machine learning algorithm 814 is implemented using a neural network algorithm (e.g. a recurrent neural network), the feature engineering blocks 806 and 826 are optional and are, instead, intrinsically performed by the neural network algorithm that implements the machine learning algorithm 814. However, in cases where the machine learning algorithm 814 is implemented using a random forest algorithm or a support vector machine algorithm, the feature engineering blocks 806 and 826 may be needed. Such aspects are discussed in further detail below in reference to FIGS. 9A and 9B. When the feature engineering blocks 806 and 826 are needed, during the iterative optimization of stored feature vectors 810, a number of parameters of feature engineering 806 may be updated. Examples of feature engineering parameters that may be updated using the machine learning process include but are not limited to: the number of chirps being averaged during the calculation of the range FFT and/or the azimuth FFTs; the windowing and zero padding of the range FFT and/or the azimuth FFTs; the number of range points selected and polynomial order for autofocus algorithms.

Once the system has been trained using reference training data 802 that represents reference radar measurements made on a plurality of reference sites (e.g., various parts of the human body), new segmented vital-Doppler waveform live data 822 is received by embodiment millimeter-wave radar sensors during the course of identifying users and targets. Signal processing block 824 prepares the segmented vital-Doppler waveform live data 822 for feature engineering, and the feature engineering block 826 forms new extracted feature vectors 728. Prediction model 830 utilizes machine learning algorithm 814 to match new extracted feature vectors 828 to a stored feature vector 810. When a match is identified a predicted label is provided that identifies the new feature vector. In some embodiments, data from the stored labels 812 is provided as a predicted emotion label (e.g. talking, anger, scared, crying, tenderness, laughing, anxious). Prediction model 830 may be a machine learning model with optimal parameters computed/evaluated through a machine learning algorithm.

Figure 9A:
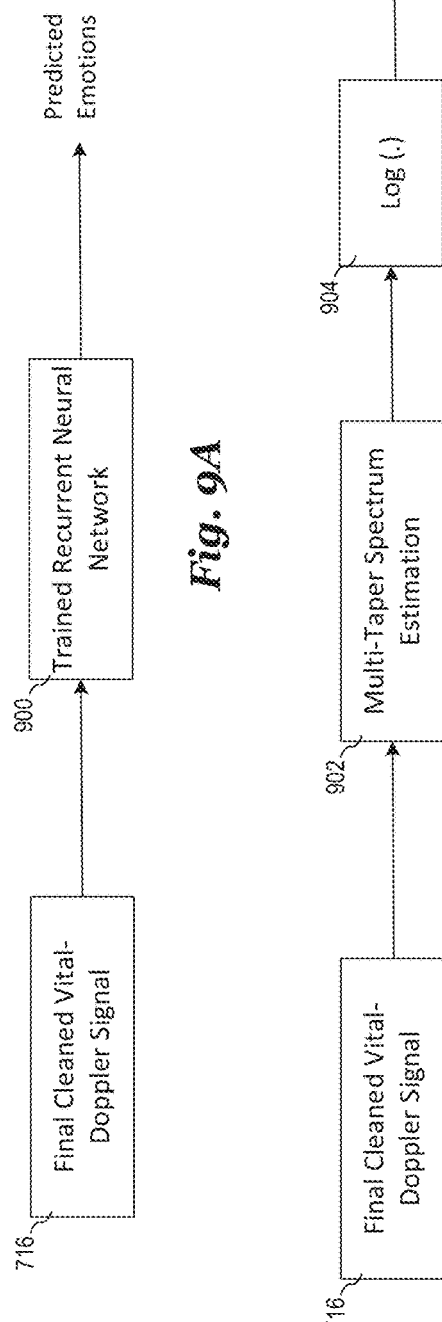
FIG. 9A shows an embodiment where a recurrent neural network is used to implement at least a portion of the prediction step shown in FIG. 8.

FIG. 9A shows an example where a recurrent neural network (RNN) algorithm 900 is used to implement the emotion classification algorithm shown in FIG. 8. In the embodiment of FIG. 9A, since the RNN algorithm is used as the machine learning algorithm 814, the feature engineering blocks 806 and 826 may be omitted. This may be attributed to the RNN algorithm being a neural network-based deep learning algorithm that has inherent feature extraction and learning capabilities (features that are not present in other classical machine learning algorithms, such as, for example, a random forest algorithm). The ability of the RNN algorithm to learn features (and thus intrinsically implement steps 806 and 826) may be based on the architecture of the RNN. FIG. 9C shows architecture of the RNN algorithm used in the embodiment of FIG. 9A. As seen in FIG. 9C, the RNN algorithm has a many-to-one architecture that includes a plurality of input layers 901, a plurality of hidden layers 903, and a single output layer 905. As an illustration, three input layers 901 and three hidden layers 903 are shown in FIG. 9C; however, the number of input layers 901 and hidden layers 903 may be different in other embodiments. Each rectangle shown in FIG. 9C represents a vector and each arrow represents a function (e.g. a matrix-multiply operation). RNN algorithms may operate over sequences of vectors, and in the example of FIG. 9C, the input of the RNN algorithm (e.g. at the input layers 901) is sequenced according to methods known in the art. In general, for the RNN algorithm, activations in a recurrent layer at a time t are a function of the entire input sequence up to time t.

Figure 9B:
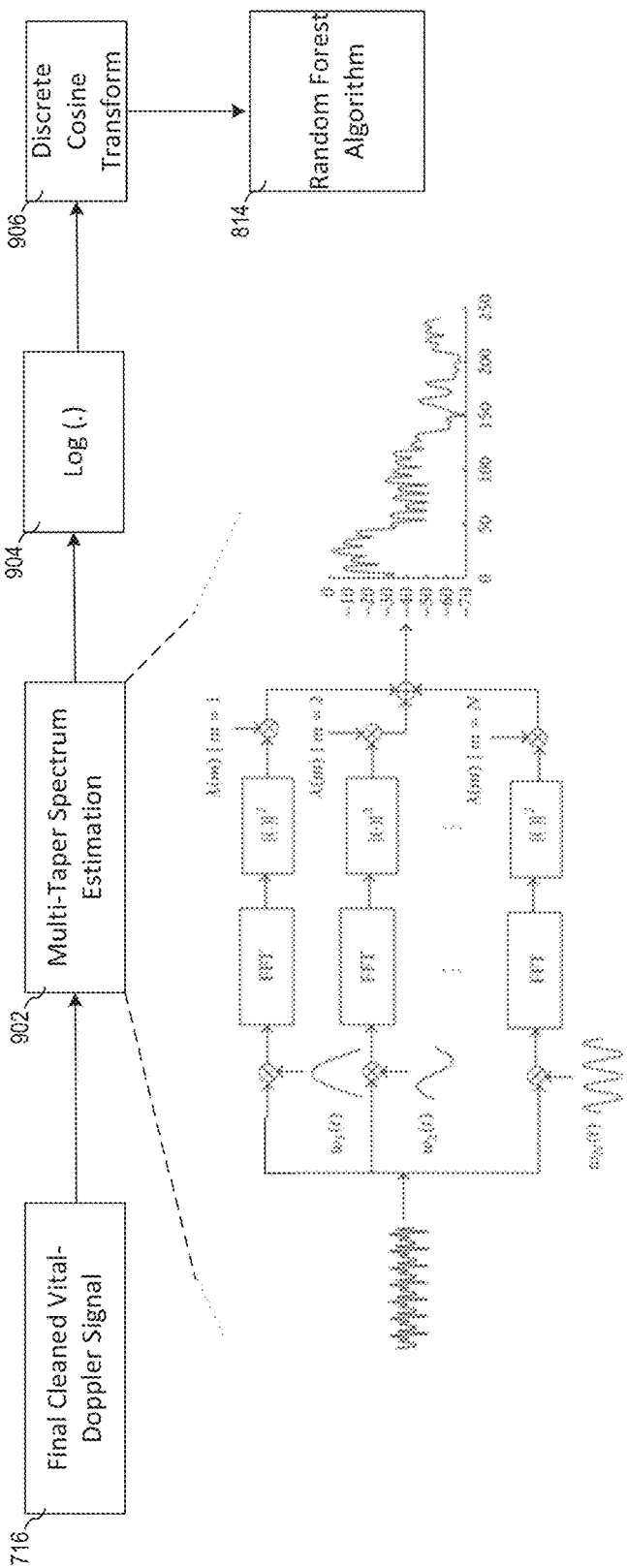
FIG. 9B shows an embodiment where a multi-taper spectrum estimation is used to implement at least a portion of the prediction step shown in FIG. 8.

FIG. 9B shows an example where a multi-taper spectrum estimation step 902 is used to implement the emotion classification algorithm shown in FIG. 8. In the example of FIG. 9B, since the random forest algorithm is used as the machine learning algorithm 814, the feature engineering blocks 806 and 826 are needed, and in FIG. 9B, the feature engineering blocks 806 and 826 are implemented using multi-taper spectrum estimation (in block 902) followed by a logarithm block 904, and a discrete cosine transform block 906. The multi-taper spectrum estimation is based on frequency ceptrum coefficient feature extraction. The multi-tapered processing depicted in FIG. 9B may be expressed as follows:

$$S_{MT}(f) = \sum_{m=1}^{N} \lambda(m) \left| \sum_{t=0}^{L-1} w_m(t)x(t)e^{-\frac{j2\pi f}{L}} \right|^2$$

where N is the number of tapers, $w_m$ is the $m^{th}$ data taper (with m=1, 2, . . . , N), and $\lambda(m)$ is the weight of the $m^{th}$ taper. Consequently, in the method depicted in FIG. 9B, spectrum estimation is obtained from a series of spectra which are weighted and averaged in the frequency domain. In estimating the spectrum by multi-tapering, the first taper attributes more weight to the center of the short-term signal than to its ends, while higher order tapers attribute increasingly more weight to the ends of the frame data. Furthermore, multi-peak multi-taper method weights can be defined as follows:

$$\lambda(m) = \frac{v_m}{\sum_{m=1}^{N} v_m} (m = 1, 2, \ldots N)$$

where $v_m$ is the eigenvalue of the $m^{th}$ window.

Figure 10A:
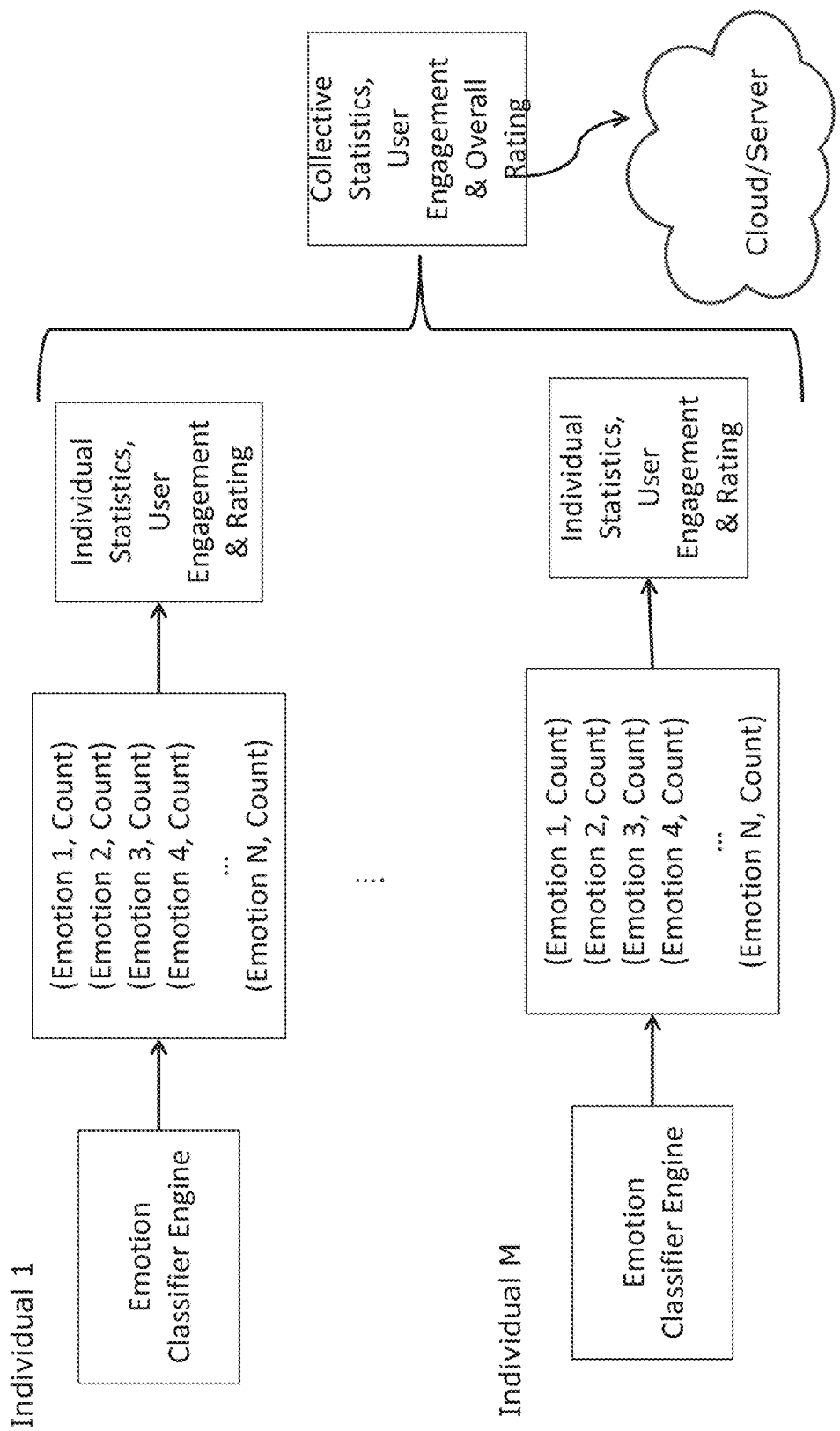
FIGS. 10A and 10B show, in greater detail, a review generation step of the method shown in FIG. 5, in accordance with various embodiments.
Figure 10B:
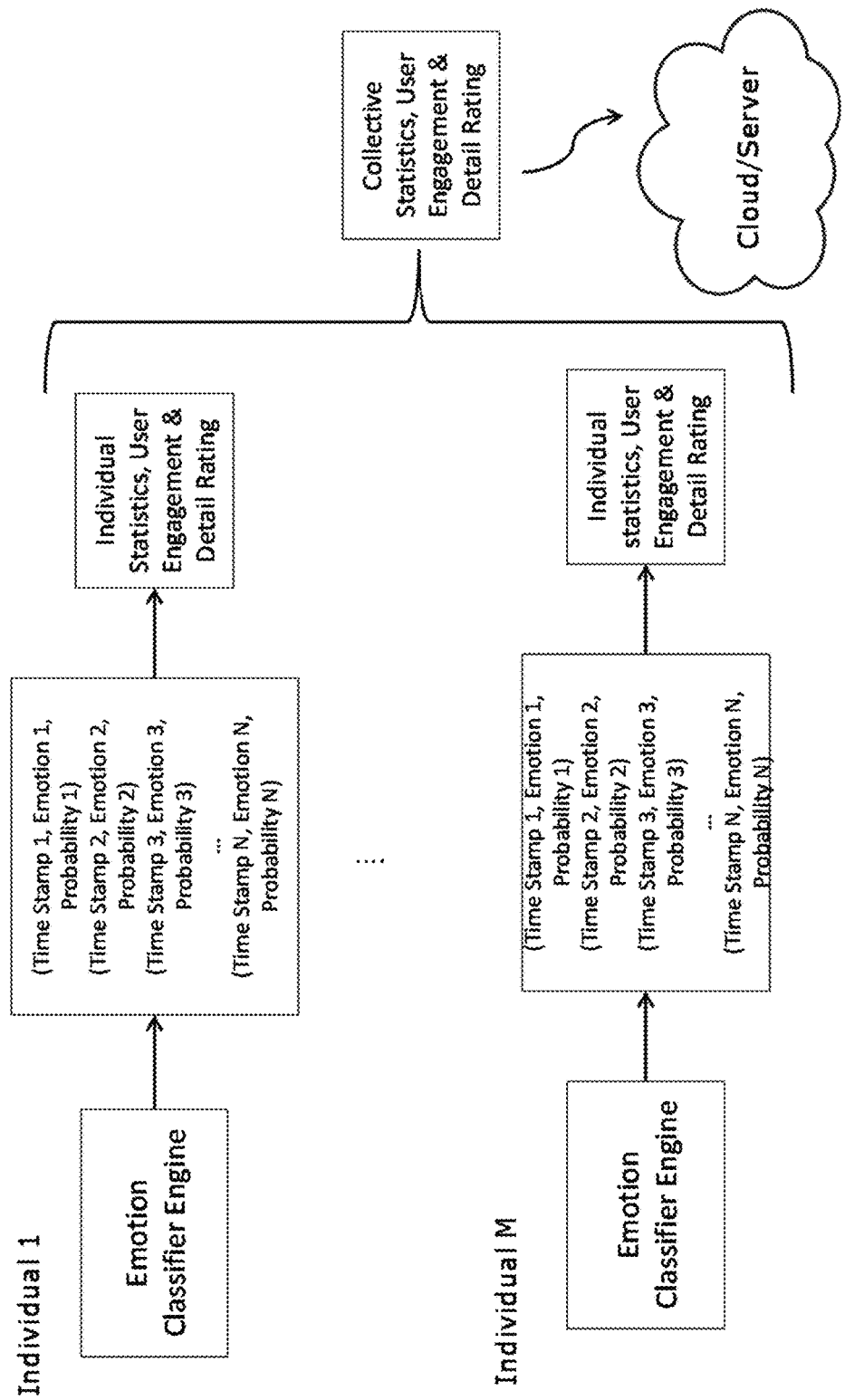

FIGS. 10A and 10B show, in greater detail, the review generation step 508 of the method 500 shown in FIG. 5, where statistics and events are recorded and a review (e.g. an overall review (as in FIG. 10A) or a detailed and particularized review (as in FIG. 10B)) is generated. Referring to FIG. 10A, M individuals are depicted, with the emotion classifier engine of FIG. 8 generating, for each respective individual, a count associated with each of the N emotions. The count associated with each of the N emotions may indicate a number of times the respective individual experienced a particular emotion within a predetermined period of time (e.g. duration of the episode, movie, game, or play). Based on the counts associated with each of the N emotions, individual statistics and a user engagement rating are generated for each individual. The individual statistics and user engagement rating for the M individuals are subsequently combined to generate collective statistics, a collective user engagement rating, and an overall rating, which may be transmitted to a network (e.g. a cloud network or a server). Such statistics, reviews, and ratings, available on the network, may be used by entities to enhance the human being's overall experience when he or she is engaged in the activity that generated the statistics, reviews, and ratings. For example, in the embodiment of FIG. 10A, an overall rating may be computed according to the following equation:

$$\sum_{i=1}^{N} w_i \text{ count}_i \geq \gamma$$

where $w_i$ indicates a weight associated with the $i^{th}$ emotion and $\text{count}_i$ indicates a number of times the $i^{th}$ emotion occurred during the predetermined period of time. In general, the weights $w_i$ are pre-decided and fixed. As an example, for a user engagement score, the weight $w_i$ associated with talking may be a negative number since the occurrence of talking during the predetermined period of time may indicate user or audience distraction. The weighted sum of the counts, $\text{count}_i$, may be compared against a threshold y, and a weighted sum greater than or equal to the threshold y may indicate that the user or audience had a positive experience while engaged in the activity in question during the predetermined period of time.

Referring to FIG. 10B, M individuals are depicted, with the emotion classifier engine of FIG. 8 generating, for each respective individual, a time stamp at which each of the N emotions occurred along with a probability that the indicated emotion at the indicated time stamp is correct. This is to be contrasted with FIG. 10A where the information generated by the emotion classifier engine indicates the number of times a particular emotion was felt by the human being, but not the time at which such emotion was felt. Based on the time stamps and probability associated with each of the N emotions, individual statistics and a user engagement rating are generated for each individual. The individual statistics and user engagement rating for the M individuals are subsequently combined to generate collective statistics, a collective user engagement rating, and an overall rating, which may be transmitted to a network (e.g. a cloud network or a server). Such statistics, reviews, and ratings, available on the network, may be used by entities to enhance the human being's overall experience when he or she is engaged in the activity that generated the statistics, reviews, and ratings. For example, in the embodiment of FIG. 10B, a detailed rating may be computed according to the following equation:

$$\sum_{time\_idx=1}^{time} w_{time\_idx}(\text{emotion}_{time\_idx}) prob_{time\_idx} \geq \gamma$$

where $\text{emotion}_{time\_idx}$ indicates the emotion estimated at time stamp time_idx, where $w_{time\_idx}$ indicates the weight associated with $\text{emotion}_{time\_idx}$, and where $prob_{time\_idx}$ indicates the probability that the indicated emotion $\text{emotion}_{time\_idx}$ at the indicated time stamp time_idx is correct. The weighted sum indicated above may be compared against a threshold y, and a weighted sum greater than or equal to the threshold y may indicate that the user or audience had a positive experience while engaged in the activity in question.

Figure 11:
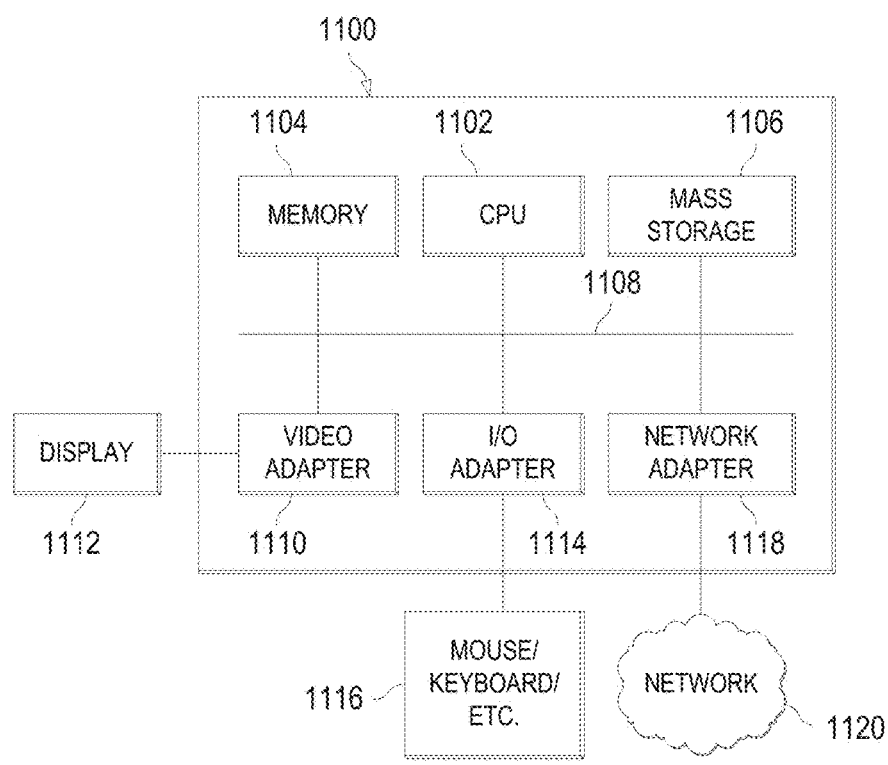
FIG. 11 illustrates a block diagram of a processing system that may be used to implement portions of embodiment radar-based detection systems.

Referring now to FIG. 11, a block diagram of a processing system 1100 is provided in accordance with an embodiment of the present invention. The processing system 1100 depicts a general-purpose platform and the general components and functionality that may be used to implement portions of the embodiment occupancy detection system and/or an external computer or processing device interfaced to the embodiment occupancy detection system. The processing system 1100 may include, for example, a central processing unit (CPU) 1102, memory 1104, and a mass storage device 1106 connected to a bus 1108 configured to perform the processes discussed above. The processing system 1100 may further include, if desired or needed, a video adapter 1110 to provide connectivity to a local display 1112 and an input-output (I/O) Adapter 1114 to provide an input/output interface for one or more input/output devices 1116, such as a mouse, a keyboard, printer, tape drive, CD drive, or the like.

The processing system 1100 also includes a network interface 1118, which may be implemented using a network adaptor configured to be coupled to a wired link, such as an Ethernet cable, USB interface, or the like, and/or a wireless/cellular link for communications with a network 1120. The network interface 1118 may also include a suitable receiver and transmitter for wireless communications. It should be noted that the processing system 1100 may include other components. For example, the processing system 1100 may include power supplies, cables, a motherboard, removable storage media, cases, and the like. These other components, although not shown, are considered part of the processing system 1100.

Figure 12:
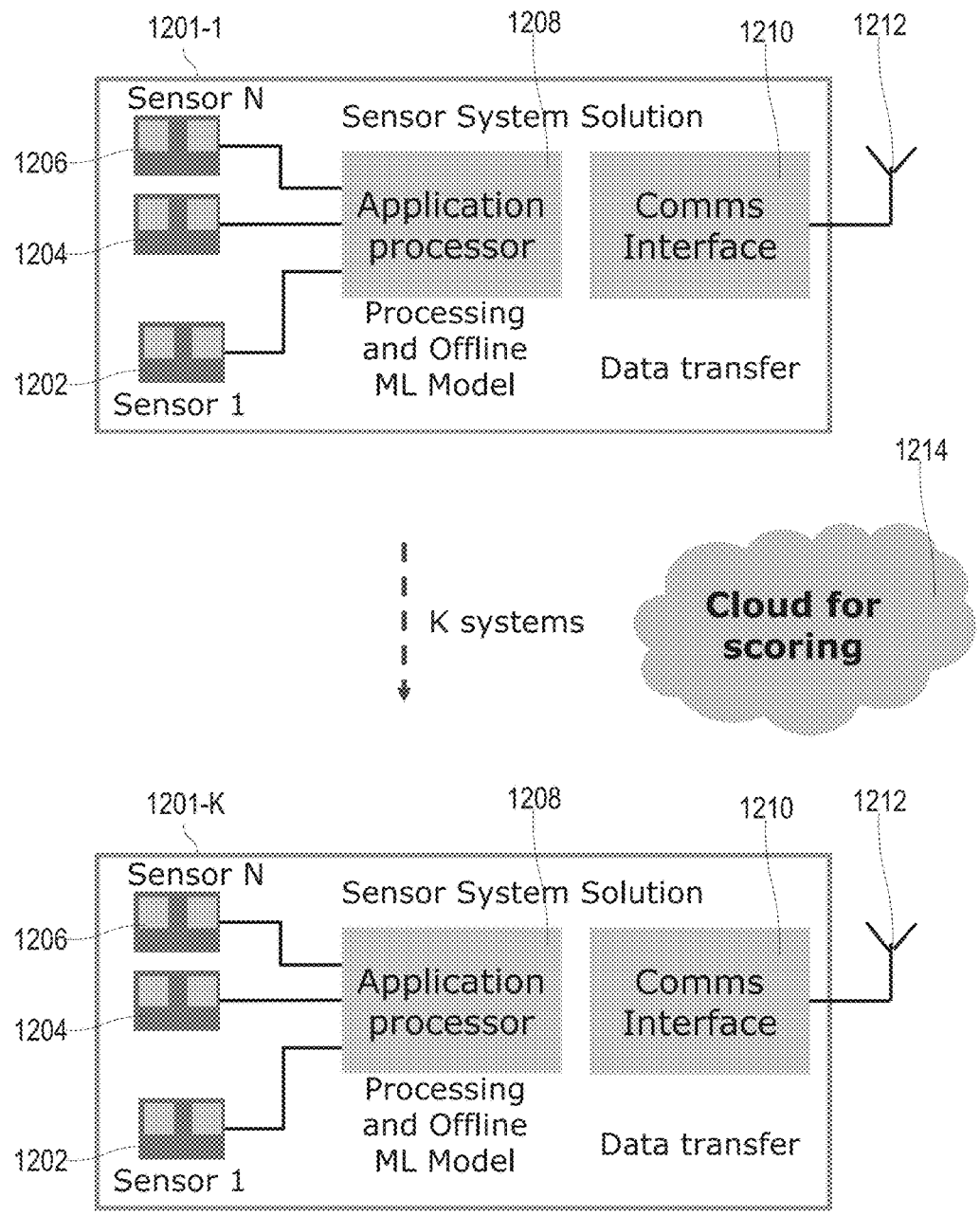
FIG. 12 shows a plurality of sensor systems that are deployed in a user space, in accordance with an embodiment.

FIG. 12 shows a plurality of sensor systems 1201-1 to 1201-K that are deployed in a user space, in accordance with an embodiment. Each sensor system of the plurality of sensor systems 1201-1 to 1201-K may, as an example, illustrate a sensor system solution deployed in a single movie or theater auditorium. As shown in FIG. 12, each sensor system of the plurality of sensor systems 1201-1 to 1201-K includes N sensors 1202, 1204, and 1206 and an application processor 1208 that processes the signals from the N sensors 1202, 1204, and 1206 (e.g. according to the aforementioned methods). Each sensor system of the plurality of sensor systems 1201-1 to 1201-K also includes a communications interface 1210, which may be coupled to an antenna 1212 that is configured to transmit the feedback of the sensor system to a network (e.g. cloud network 1214) for scoring.

The present invention will be described with respect to preferred embodiments. The present disclosure presents a system and method for determining a human being's level of engagement in a particular activity. Examples of activities that a human being may be engaged in include: viewing a movie, a play, or a television episode; listening to music; or playing a video game (e.g. an augmented reality or virtual reality video game). The determination of the human being's level of engagement in such activity may, in turn, be used to generate (e.g. automatically generate) a review or rating of the activity. Such a review or rating may be used by entities to enhance the human being's overall experience when he or she is engaged in such activity. In embodiments described herein, a human being's level of engagement in a particular activity may be determined based on the human being's heart rate and/or respiration, since respiration motion and heart rate are variable and can change in correspondence to different physical and/or emotional states, such as speaking, singing, fear, or stress. Based on such observations of the variation of respiration motion and heart rate with different physical and/or emotional states, the system and method proposed in the various embodiments disclosed herein provide a millimeter-wave radar based solution for non-intrusive determination of a human being's level of engagement in a particular activity and for non-intrusive review based on the human being's heart rate and/or respiration. The embodiments described herein automatically generate a human being's overall review of the activity based on certain metrics of overall engagement level. The embodiments also provide specific moments (e.g. window time period) where the human being was fully engaged (e.g., happy, laughing, tensed, crying, sobbing, scared) in reaction to the movie-scene, play, or game. The embodiments disclosed herein are advantageous over current solutions (e.g. electrocardiogram monitors and/or wearable systems) in that the embodiments do not cause discomfort to the human being, are accurate in measuring or determining respiration, and allow the human being to breathe normally or spontaneously (thereby allowing for accurate assessment of heart rate, respiration, and level of engagement).

An embodiment method may include receiving radar data at a millimeter-wave radar sensor, the radar data being generated in response to an incident radio-frequency signal reflecting off a biological target located in a field of view of the millimeter-wave radar sensor; extracting a filtered vital-Doppler signal from the radar data; determining an emotion of the biological target based on the filtered vital-Doppler signal; and generating a user-engagement rating indicative of a level of engagement of the biological target in an activity performed in the field of view based on the emotion.

An embodiment system may include a processing system configured to be coupled to a millimeter-wave radar sensor. The processing system may be configured to: instruct the millimeter-wave radar sensor to transmit a series of chirps within a field of view of the millimeter-wave radar sensor; identify a set of targets within the field of view based on radar data received by the millimeter-wave radar sensor and in response to transmission of the series of chirps; extract a filtered vital-Doppler signal from the radar data; determine an emotion of the set of targets based on the filtered vital-Doppler signal; and generate a user-engagement rating indicative of a level of engagement of the set of targets in an activity performed in the field of view based on the emotion.

An embodiment non-transitory computer readable storage medium has an executable program stored thereon. The executable program may include instructions to: instruct a millimeter-wave radar sensor to transmit a series of chirps within a field of view of the millimeter-wave radar sensor; identify a biological target within the field of view based on radar data received by the millimeter-wave radar sensor and in response to transmission of the series of chirps; extract a filtered vital-Doppler signal from the radar data; determine an emotion of the biological target based on the filtered vital-Doppler signal; and generate a user-engagement rating indicative of a level of engagement of the biological target in an activity performed in the field of view based on the emotion.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method, comprising:
    receiving radar data at a millimeter-wave radar sensor, the radar data being generated in response to an incident radio-frequency signal reflecting off a biological target located in a field of view of the millimeter-wave radar sensor;
    extracting a filtered vital-Doppler signal from the radar data, wherein extracting the filtered vital-Doppler signal from the radar data comprises:
        capturing the radar data corresponding to the biological target across a vital-Doppler frame;
        performing a first filtering on the vital-Doppler frame to produce a first-filtered vital-Doppler frame; and
        performing a second filtering on the vital-Doppler frame to produce a second-filtered vital-Doppler frame;
        designating at least one of the first-filtered vital-Doppler frame or the second-filtered vital-Doppler frame as a time-domain vital-Doppler signal;
        filtering the time-domain vital-Doppler signal with a window function that is localized in time and frequency to generate a windowed time-frequency signal, the filtering the time-domain vital-Doppler signal comprising convolving the time-domain vital-Doppler signal with the window function;
        determining initial filter coefficients of a frequency filter;
        performing a Gabor time-frequency transform on the windowed time-frequency signal;
        filtering a result of the Gabor time-frequency transform step using the frequency filter having the initial filter coefficients;
        performing an inverse Gabor time-frequency transform on an output of the frequency filter to generate an interim filtered vital-Doppler signal;
        determining a ratio of an out-of-band energy of the interim filtered vital-Doppler signal to a total energy of the interim filtered vital-Doppler signal; and
        in response to the ratio being greater than a threshold, iteratively performing the following steps:
            selecting new filter coefficients of the frequency filter based on a predetermined sequence of filter coefficients;
            performing the Gabor time-frequency transform;
            filtering the result of the Gabor time-frequency transform step using the frequency filter having the new filter coefficient; and
            performing the inverse Gabor time-frequency transform;
    determining an emotion of the biological target based on the filtered vital-Doppler signal; and
    generating a user-engagement rating indicative of a level of engagement of the biological target in an activity performed in the field of view based on the emotion.

2. The method of claim 1, wherein determining the emotion of the biological target based on the filtered vital-Doppler signal comprises:
    determining a number of times a respective emotion of a plurality of emotions occurred during the activity.

3. The method of claim 2, wherein generating the user-engagement rating comprises:

generating the user-engagement rating based on the plurality of emotions and the number of times each of the plurality of emotions occurred during the activity.

4. The method of claim 1, wherein determining the emotion of the biological target based on the filtered vital-Doppler signal comprises:
   determining a time instance at which a respective emotion of a plurality of emotions occurred during the activity; and
   determining a probability of the respective emotion occurring at the time instance.

5. The method of claim 4, wherein generating the user-engagement rating comprises:
   generating the user-engagement rating based on the plurality of emotions, the time instance associated with each of the plurality of emotions, and the probability associated with each of the plurality of emotions.

6. The method of claim 1, wherein determining the emotion of the biological target based on the filtered vital-Doppler signal comprises determining respective emotions of each of a plurality of biological targets based on the filtered vital-Doppler signal.

7. The method of claim 6, wherein generating the user-engagement rating indicative of the level of engagement of the biological target in the activity based on the emotion comprises generating a respective user-engagement rating indicative of a respective level of engagement of each of the plurality of biological targets based on the respective emotions of each of the plurality of biological targets.

8. The method of claim 7, further comprising generating a collective statistic indicative of the level of engagement of the plurality of biological targets based on the respective user-engagement ratings.

9. The method of claim 1, wherein the first filtering comprises a band-pass filtering centered at 0.8 Hz with a bandwidth of 0.6 Hz.

10. The method of claim 1, wherein the second filtering comprises a band-pass filtering centered at 2 Hz with a bandwidth of 3 Hz.

11. The method of claim 1, wherein a result of the inverse Gabor time-frequency transform is designated as the filtered vital-Doppler signal in response to the ratio being less than the threshold.

12. The method of claim 1, wherein the out-of-band energy of the interim filtered vital-Doppler signal comprises an energy of the interim filtered vital-Doppler signal outside a frequency range of 0.6 Hz to 5 Hz.

13. The method of claim 1, wherein determining the emotion of the biological target based on the filtered vital-Doppler signal comprises:
   performing a set of reference radar measurements for a plurality of reference emotion labels on the biological target using the millimeter-wave radar sensor;
   producing a training data set for the plurality of reference emotion labels based on the set of reference radar measurements;
   forming a set of stored feature vectors based on the training data set; and
   associating a respective emotion label to each stored feature vector of the set of stored feature vectors.

14. The method of claim 13, wherein forming the set of stored feature vectors comprises iteratively adjusting the forming of the set stored feature vectors using a machine learning algorithm.

15. The method of claim 14, wherein determining the emotion of the biological target based on the filtered vital-Doppler signal comprises:
   extracting live feature vectors from the filtered vital-Doppler signal; and
   determining the emotion of the biological target based on the live feature vectors and the set stored feature vectors using the machine learning algorithm.

16. A system, comprising:
a processing system configured to be coupled to a millimeter-wave radar sensor, wherein the processing system is configured to:
   instruct the millimeter-wave radar sensor to transmit a series of chirps within a field of view of the millimeter-wave radar sensor;
   identify a set of targets within the field of view based on radar data received by the millimeter-wave radar sensor and in response to transmission of the series of chirps;
   extract a filtered vital-Doppler signal from the radar data, wherein extracting the filtered vital-Doppler signal from the radar data comprises:
      capturing the radar data corresponding to the set of targets across a vital-Doppler frame;
      performing a first filtering on the vital-Doppler frame to produce a first-filtered vital-Doppler frame; and
      performing a second filtering on the vital-Doppler frame to produce a second-filtered vital-Doppler frame;
      designating at least one of the first-filtered vital-Doppler frame or the second-filtered vital-Doppler frame as a time-domain vital-Doppler signal;
      filtering the time-domain vital-Doppler signal with a window function that is localized in time and frequency to generate a windowed time-frequency signal, the filtering the time-domain vital-Doppler signal comprising convolving the time-domain vital-Doppler signal with the window function;
      determining initial filter coefficients of a frequency filter;
      performing a Gabor time-frequency transform on the windowed time-frequency signal;
      filtering a result of the Gabor time-frequency transform step using the frequency filter having the initial filter coefficients;
      performing an inverse Gabor time-frequency transform on an output of the frequency filter to generate an interim filtered vital-Doppler signal;
      determining a ratio of an out-of-band energy of the interim filtered vital-Doppler signal to a total energy of the interim filtered vital-Doppler signal; and
      in response to the ratio being greater than a threshold, iteratively performing the following steps:
         selecting new filter coefficients of the frequency filter based on a predetermined sequence of filter coefficients;
         performing the Gabor time-frequency transform;
         filtering the result of the Gabor time-frequency transform step using the frequency filter having the new filter coefficient; and
         performing the inverse Gabor time-frequency transform;
   determine an emotion of the set of targets based on the filtered vital-Doppler signal; and
   generate a user-engagement rating indicative of a level of engagement of the set of targets in an activity performed in the field of view based on the emotion.

17. A non-transitory computer readable storage medium with an executable program stored thereon, the executable program including instructions to:
  instruct a millimeter-wave radar sensor to transmit a series of chirps within a field of view of the millimeter-wave radar sensor;
  identify a biological target within the field of view based on radar data received by the millimeter-wave radar sensor and in response to transmission of the series of chirps;
  extract a filtered vital-Doppler signal from the radar data, wherein extracting the filtered vital-Doppler signal from the radar data comprises:
    capturing the radar data corresponding to the biological target across a vital-Doppler frame;
    performing a first filtering on the vital-Doppler frame to produce a first-filtered vital-Doppler frame; and
    performing a second filtering on the vital-Doppler frame to produce a second-filtered vital-Doppler frame;
    designating at least one of the first-filtered vital-Doppler frame or the second-filtered vital-Doppler frame as a time-domain vital-Doppler signal;
    filtering the time-domain vital-Doppler signal with a window function that is localized in time and frequency to generate a windowed time-frequency signal, the filtering the time-domain vital-Doppler signal comprising convolving the time-domain vital-Doppler signal with the window function;
    determining initial filter coefficients of a frequency filter;
    performing a Gabor time-frequency transform on the windowed time-frequency signal;
    filtering a result of the Gabor time-frequency transform step using the frequency filter having the initial filter coefficients;
    performing an inverse Gabor time-frequency transform on an output of the frequency filter to generate an interim filtered vital-Doppler signal;
    determining a ratio of an out-of-band energy of the interim filtered vital-Doppler signal to a total energy of the interim filtered vital-Doppler signal; and
    in response to the ratio being greater than a threshold, iteratively performing the following steps:
      selecting new filter coefficients of the frequency filter based on a predetermined sequence of filter coefficients;
      performing the Gabor time-frequency transform;
      filtering the result of the Gabor time-frequency transform step using the frequency filter having the new filter coefficient; and
      performing the inverse Gabor time-frequency transform;
  determine an emotion of the biological target based on the filtered vital-Doppler signal; and
  generate a user-engagement rating indicative of a level of engagement of the biological target in an activity performed in the field of view based on the emotion.

* * * * *